Figure 1:
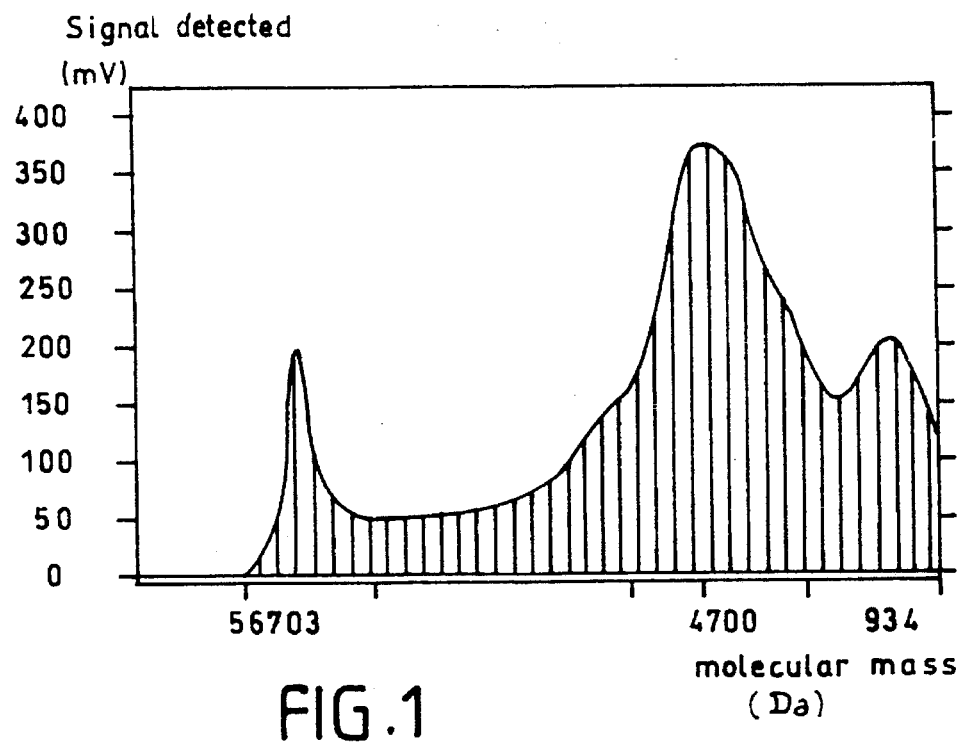

United States Patent [19]
Lormeau et al.

[11] Patent Number: 5,550,116
[45] Date of Patent: Aug. 27, 1996

[54] N,O-SULPHATED HEPAROSANS AND PHARMACEUTICAL COMPOSITIONS CONTAINING THEM

[75] Inventors: Jean Claude Lormeau, Kremlin Bicetre; Bruno Chevallier, Paris; Marc L. V. Salomé, Castanet-Tolosan; Guy E. M. Tenaille d'Estais, Toulouse, all of France

[73] Assignee: Sanofi, Paris, France

[21] Appl. No.: 389,618

[22] Filed: Feb. 15, 1995

Related U.S. Application Data

[63] Continuation of Ser. No. 266,302, Jun. 27, 1994, abandoned, which is a continuation of Ser. No. 801,923, Dec. 3, 1991, abandoned.

[30] Foreign Application Priority Data

Dec. 3, 1990 [FR] France ................................. 90 15114

[51] Int. Cl.$^6$ ................................................. A61K 31/725
[52] U.S. Cl. ........................... 514/56; 514/53; 514/54; 536/21; 536/53; 536/54; 536/55; 536/55.1; 536/55.2
[58] Field of Search .................. 536/21, 53, 54, 536/55, 55.1, 55.2; 514/53, 54, 56

[56] References Cited

U.S. PATENT DOCUMENTS

| | | | |
|---|---|---|---|
| 3,211,616 | 10/1965 | Yosizawa | 536/55.1 |
| 4,727,063 | 2/1988 | Naggi et al. | 514/56 |
| 4,816,446 | 3/1989 | Feller et al. | 514/56 |
| 4,990,502 | 2/1991 | Lormeau et al. | 514/56 |
| 5,008,253 | 4/1991 | Casu et al. | 514/54 |
| 5,013,724 | 5/1991 | Petitou et al. | 514/54 |
| 5,071,969 | 12/1991 | Van Boeckel et al. | 536/123.1 |

FOREIGN PATENT DOCUMENTS

| | | |
|---|---|---|
| 0116801 | 8/1984 | European Pat. Off. . |
| 0287477 | 10/1988 | European Pat. Off. . |
| 0333243 | 9/1989 | European Pat. Off. . |
| 0356275 | 2/1990 | European Pat. Off. . |
| 2584728 | 1/1987 | France . |
| 206697 | 10/1986 | New Zealand . |
| 226835 | 3/1989 | New Zealand . |
| 228271 | 5/1991 | New Zealand . |
| 230041 | 9/1991 | New Zealand . |

OTHER PUBLICATIONS

Gupta et al; FEMS Microbiol. Lett. 16:13–17 (1983).
Atha et al; Biochem. 26:6454–61 (1987).
Sugahara et al; Biochem. Biophys. Res. Commun. 162(1):189–197 (1989).
Bashkin et al; Biochem. 28:1737–43 (1989).
Platt et al; Dev. Biol. 139:338–48 (1990).
Hurley et al; Chemical Abstracts 114:239930n (1991).
Lindahl et al; J. Biol. Chem. 248(20):7234–41 (1973).
Nagasawa et al; J. Biochem. 81:989–993 (1977).
Linker; Biochem. J. 183:711–720 (1979).
Riesenfeld et al; J. Biol. Chem. 255(3):922–8 (1980).
Sjöberg et al; Biochem. J. 191:103–110 (1980).
Vann et al; Eur. J. Biochem. 116:359–364 (1981).
The Merck Index 10th Ed. pp. 672–673 #4543 (1983).
Sanderson et al; Biochem. J. 211:677–682 (1983).
J. L. Navia et al., "Assay of N–Acetylheparosan Deacetylase with a Capsular Polysaccharide from *Escherichia coli* K5 as Substrate", Analytical Biochemistry, vol. 135, 1983, pp. 134–140.

*Primary Examiner*—Gary L. Kunz
*Assistant Examiner*—Kathleen Kahler Fonda
*Attorney, Agent, or Firm*—Jacobson, Price, Holman & Stern, PLLC

[57] ABSTRACT

The invention relates to N,O-sulphated heparosans consisting of chains or of a mixture of chains of molecular mass between 1500 and 15,000 Da, characterized by a repeated disaccharide structure of formula I:

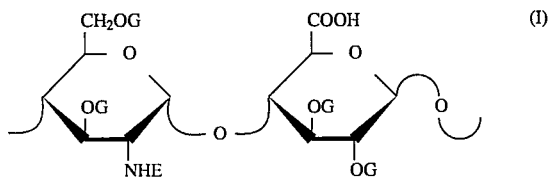

in which:

E represents an acetyl group in 0 to 80% of the disaccharide units of the said N,O-sulphated heparosan, and a sulphate group and possibly a hydrogen atom in the remaining disaccharide units, G represents a hydrogen atom and a sulphate group, and the pharmaceutically acceptable salts of the
said N,O-sulphated heparosans. The heparosans are useful as anticoagulants.

18 Claims, 3 Drawing Sheets

N,O-SULPHATED HEPAROSANS AND PHARMACEUTICAL COMPOSITIONS CONTAINING THEM

This application is a file wrapper continuation application Ser. No. 08/266,302, filed Jun. 27, 1994, now abandoned, which is a file wrapper continuation of application Ser. No. 07/801,923, filed Dec. 3, 1991, now abandoned.

The present invention relates to new N,O-sulphated heparosans, to compositions of N,O-sulphated heparosans containing these new N,O-sulphated heparosans and to pharmaceutical compositions having the new N,O-sulphated heparosans as an active principle.

It is known that glycosaminoglycans are products capable of being obtained by extraction of animal tissues. Some of these glycosaminoglycans possess very advantageous anticoagulant and antithrombotic properties. Typical products of this family are heparin, its fragments and their derivatives, as well as heparan sulphate and dermatan sulphate, which have, however, the disadvantage, owing to their origin, of being very expensive.

In particular, it is known that dermatan sulphate is a family of polymers with a variable degree of polymerisation, composed of repeated units consisting of a uronic acid group (iduronyl or glucuronyl) and an acetyl-4-sulphogalactosaminyl group (H. W. Stuhlsatz "The Methodology of Connective Tissue Research", (1976), 137–146). Natural dermatan sulphate has a molecular mass of between 20,000 and 40,000 Da. This product is especially advantageous as an anticoagulant and antithrombotic (F. Fernandez et al, British Journal of Haematology, (1986), 64, 309–317).

It is, furthermore, known (I. Björk and U. Lindahl, "Molecular and Cellular Biochemistry", (1982), Dr. W. Junk Publishers—Holland) that blood coagulation is a complex physiological phenomenon whose mechanism may be summarised diagrammatically as follows:

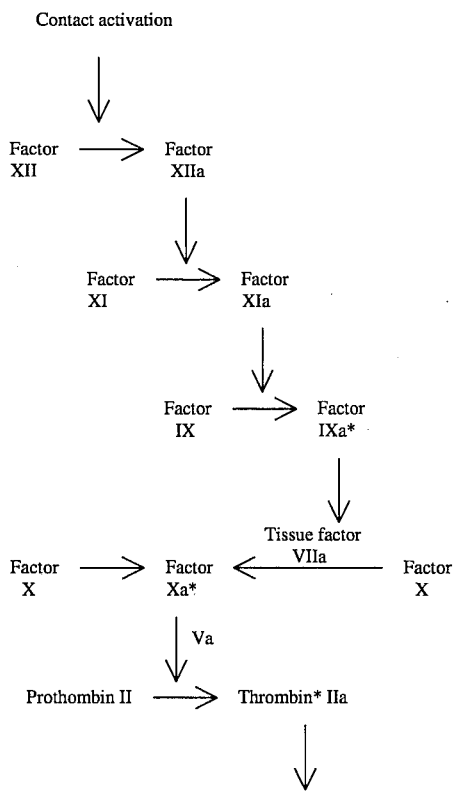

Certain stimuli, such as contact activation and tissue factors, trigger the successive activation of a series of coagulation factors present in blood plasma, these being identified by roman numerals on the above diagram and the presence of the index a denoting the activated form (index a present) or unactivated form (index a absent) of a given coagulation factor.

Irrespective of the nature of the stimulus, the final steps are identical, factor Xa activates factor II (also known as prothrombin), which, in its activated form (factor IIa, also known as thrombin), causes partial proteolysis of the soluble fibrinogen with release of insoluble fibrin, the main constituent of the blood clot.

Under normal physiological conditions, regulatory proteins such as antithrombin III (ATIII) and heparin cofactor II (HCII) are also present in plasma.

Antithrombin III exercises an inhibitory activity with respect to all the coagulation factors identified by an asterisk (*) in the above diagram. This inhibition is very strongly amplified in the presence of heparin or of synthetic oligosaccharides of the heparin type (D. H. Atha et al, Biochemistry, (1985), 24, 6723–6729).

Heparin cofactor II exercises an inhibitory activity only with respect to factor IIa (thrombin), which catalyses the last step in coagulation. This activity is greatly amplified in the presence of heparin or of dermatan sulphate (D. M. Tollefsen, J. Biol. Chem, (1983), 258, 6713–6716).

Inhibition of factor Xa or of factor IIa constitutes a favoured means for obtaining anticoagulant and antithrombotic activity, since these two factors participate in the last two steps in coagulation, which are independent of the triggering stimulus.

To obtain inhibition of factor IIa alone, an especially advantageous possibility consists in taking advantage of the specificity of heparin cofactor II and endeavouring to amplify its inhibitory activity. Dermatan sulphate is the known product possessing the most potent amplificatory activity of this type.

It is also known that formation of the main heparin chain takes place in two steps. Initially, heparin is biosynthesised from a proteoglycan precursor, the polysaccharide portion of which consists of a family of polymers with a variable degree of polymerisation, composed of repeated β-D-glucuronyl-(1→4)-α-N-acétyl-α-D-glucosaminyl-(1→4)-units (disaccharide units) of molecular mass 379 Da. This polysaccharide portion is usually referred to as N-acetylheparosan (J. Navia, Anal. Biochem., (1983), 135, 134–140). This first step of biosynthesis represents the only point at which it is genuinely possible to speak of a "disaccharide unit", since the second step of the biosynthesis will bring about a profound modification of this simple skeleton ("L∝héparine, fabrication, structure, propriétés, analyses" (Heparin, manufacture, structure, properties, analyses), J. P. Duclos, (1984) pp 81–83, Masson Ed.-France).

In effect, natural heparin resulting from biosynthesis is a polysaccharide consisting of molecules of glucuronic acid and iduronic acid (uronic acids), possibly sulphated at position 2, combined with molecules of glucosamine, possibly sulphated at position 6 and sulphated or acetylated on the amine at position 2.

The structure of heparin may be represented statistically by the following formula (i):

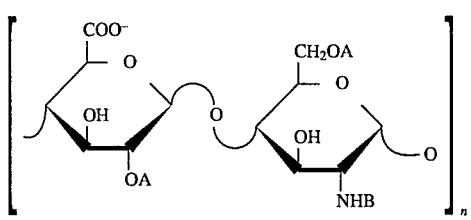

where A represents H and $SO_3^-$, B represents $SO_3^-$ and $COCH_3$ and n is an integer between 20 and 30, corresponding to a molecular weight of 12,000 to 18,000 Da (EP-A-0,116,801).

The expressions "H and $SO_e^-$" and "$SO_3^-$ and $COCH_3$", as used, respectively, for the substituents A and B, indicate that, in the 20 to 30 disaccharide units above, A is hydrogen in some cases and an $SO_3^-$ group in other cases, and, likewise, B is $SO_3^-$ in the majority of cases and an acetyl group in other cases.

Similarly, the } that the $COO^-$ group in the 20 to 30 disaccharide units above has, in some cases, the configuration (ii):

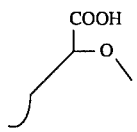

(corresponding to D-glucuronic acid)
and, in the majority of the n units, the configuration (iii):

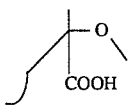

(corresponding to L-iduronic acid).

Hence, heparin and the heparin fragments as obtained by various depolymerisation methods are macromolecules containing both glucuronic acid units and iduronic acid units.

Some depolymerisation methods enable heparin fragments having a molecular weight of between 2000 and 9000 Da and a degree of sulphation at least 20% greater than that of the heparin starting material to be obtained. Such "supersulphated" heparins are described in Patent Application EP-A-0,116,801, and possess, as regards the uronic acid units, the two structures (ii) and (iii) mentioned above.

It is also known that some bacteria of the species *Escherichia coli* produce a capsular polysaccharide, usually referred to as the K5 antigen, which is a family of polymers consisting of repeated β-D-glucuronyl-(1→4)-α-N-acetyl-D-glucosaminyl(1.4)-units (W. F. Vann et al, Eur. J. Biochem, (1981), 116,359–364).

This polysaccharide, of the same chemical nature as the polysaccharide portion of the proteoglycan precursor of heparin, will be referred to here as N-acetylheparosan. This product possesses a molecular mass of between $10^5$ and $2 \times 10^6$ Da and, in respect of the "uronic acid" units, a very regular structure composed exclusively of D-glucuronic acid (W. F. Vann et al, Eur. J. Biochem., (1981), 116, 359–364, and Patent Application EP-A-0,333,243).

Patent Application EP-A-0,333,243 describes the O-sulphated K5 polysaccharide, as well as some of its fragments composed of 4, 6 or 8 "sugar" units, respectively, also 0-sulphated. These products have antiangiogenic and antitumour activity, with a favourable ratio of these activities relative to the anticoagulant properties. This document also describes N-acetylheparosan fragments composed of 4, 6, 8 or 10 "sugar" units, respectively.

Patent Application EP-A-0,333,243 also describes the preparation, by total chemical synthesis, of a pentasaccharide having the O-sulphated N-acetylheparosan structure.

It has now been found that N,O-sulphated heparosans with a variable molecular weight of between 1,500 and 15,000 Da possess anticoagulant activity with respect to heparin cofactor II and very high anti-Xa activity.

The N,O-sulphated heparosans which are the subject of the present invention are hence distinguished from the other products already described in the literature, by their novel structure, in particular their degree of sulphation (sulphation also on the amine group of the glucosamine), and their pharmacological properties. They possess, among other pharmacological properties, a stronger anticoagulant activity with respect to heparin cofactor II (HCII) than that of dermatan sulphate, and they have very advantageous pharmacokinetic characteristics. In effect, the products of the invention, which are products obtained by partial chemical synthesis, possess the pharmacological activities of the glycosaminoglycans commonly used therapeutically, in particular those of heparin, and they may be useful for the regulation of coagulation and may, more especially, find application as antithrombotics.

The subject of the present invention is N,O-sulphated heparosans consisting of chains or of a mixture of chains of molecular mass between 1,500 and 15,000 Da, characterised by a repeated disaccharide structure of formula I:

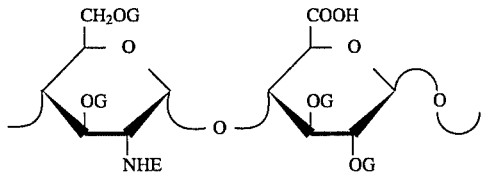

in which:

E represents an acetyl group in 0 to 80% of the disaccharide units of the said N,O-sulphated heparosans, and sulphate group and possibly a hydrogen atom in the remaining disaccharide units, G represents a hydrogen atom and a sulphate group, and the pharmaceutically acceptable salts of the said N,O-sulphated heparosans.

The degree of sulphation of the N,O-sulphated heparosans, expressed as the sulphate/carboxyl ratio, is preferably 1.5 to 3.0.

The invention also relates to a composition of N,O-sulphated heparosan containing at least 70% by mass of an N,O-sulphated heparosan described above and which is the subject of the present invention, and preferably containing at least 90% by mass of an N,O-sulphated heparosan which is the subject of the present invention.

The N,O-sulphated heparosans which are the subject of the present invention can consist of identical polysaccharide chains of well-defined molecular mass, this molecular mass lying within the range 1,500–15,000 Da. They can also consist of a mixture of chains of variable molecular masses, these molecular masses being between 1,500 and 15,000 Da. The dispersion of the molecular masses of these chains can be larger or smaller. In effect, the N,O-sulphated heparosans which are the subject of the present invention can consist of chains having between them a difference in molecular mass of at most approximately 13,500 Da, or, on the contrary, only of chains having between them a difference in molecular weight of approximately 300 Da, corresponding to one unit of uronic structure (D-glucuronic acid or its derivatives) or of glucosamine structure. It is also obvious that, depending on the constitution of each N,O-sulphated heparosan, the molecular mass of the chains having either the lowest molecular mass or the highest molecular mass can correspond to any value between 1,500 and 15,000 Da.

The expression "G represents a hydrogen atom and a sulphate group" used above indicates that G in the disaccharide unit represents a hydrogen atom for some positions and a sulphate group in the other, remaining positions. Similarly, E represents an acetyl group in some disaccharide units and a sulphate group or possibly a hydrogen atom in the remainder of these units. The disaccharide units of the N,O-sulphated heparosans are hence not all identical.

The formula I represents a repetitive disaccharide structure composed of a glucosamine unit and a D-glucuronic acid unit. The said units can be reversed, more especially if it is considered that the disaccharide structure of formula I is repeated n times, and that the non-reducing unit of the chains can equally well be either a glucosamine unit, as shown in formula I with a hydroxyl group at position 4, this glucosamine unit being sulphated or otherwise, or a D-glucuronic acid possibly containing a double bond at position C4-C5 and being sulphated or otherwise. The reducing unit can equally well be either a D-glucuronic acid, as shown in formula I, substituted with a hydrogen on the anomeric oxygen, or a glucosamine, or a 2,5-anhydromanno structure as obtained as a consequence of a nitrous depolymerisation (2,5-anhydro-D-mannose) optionally followed by an oxidation (2,5-anhydro-D-mannonic acid) or a reduction (2,5-anhydro-D-mannitol).

Preferred products are those in which the two ends, reducing and non-reducing, of the chains of the N,O-sulphated heparosans which are the subject of the present invention are uronic units, sulphated or otherwise, glucosamine units, sulphated or otherwise, N-acetylglucosamine units, sulphated or otherwise, or units having a 2,5-anhydromanno structure.

N,O-Sulphated heparosans consisting of chains in which the two ends, reducing and non-reducing, are uronic units, sulphated or otherwise, glucosamine units, sulphated or otherwise, and N-acetylglucosamine units, sulphated or otherwise, are preferred.

The subject of the present invention is also a process for preparing a composition containing 70% to 100% of an N,O-sulphated heparosan which is the subject of the present invention, characterised in that it comprises the following sequence of steps:

step a: culture of an *Escherichia coli* (K5) strain to form an N-acetylheparosan, step b: isolation and purification of the N-acetylheparosan formed to obtain a composition containing 70% to 100% of an N-acetylheparosan consisting of chains or of a mixture of chains of molecular mass between 1,500 and 15,000 Da, characterised by a repeated disaccharide structure of formula II:

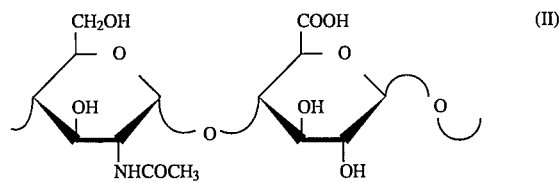

step c: partial deacetylation of this composition of N-acetylheparosan to obtain a composition containing 70% to 100% of a heparosan consisting of chains or of a mixture of chains of molecular mass between 1,500 and 15,000 Da, characterised by a repeated disaccharide structure of formula III:

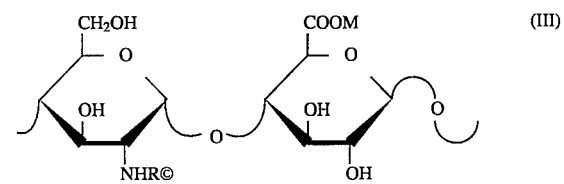

in which R' represents an acetyl group in 0 to 80% of the disaccharide units, and a hydrogen atom in the remaining disaccharide units, step d: either partial N,O-sulphation of this composition of heparosan, or partial N,O-sulphation of this composition of heparosan followed by a step of total N-sulphation, or a total or partial N-sulphation followed by a step of total or partial 0-sulphation, and optionally entails one or more steps of fractionation of the molecular masses, formed at the end of steps a, b, c or d.

For the preparation of a composition containing 70% to 100% of an N,O-sulphated heparosan which is the subject of the present invention, and according to the process of the invention, *Escherichia coli* strain SEBR 3282 is preferably used as the Escherichia coli (K5) strain. This strain is a strain derived from the strain Bi 8337–41 (010: K5: H4) ATCC 23506 (described, in particular, by D. S. Gupta et al FEMS Microbiology Letters, (1982), 14, 75–78 and W. Vann Eur. J. Biochem., (1981), 116, 359–364).

*Escherichia coli* strain SEBR 3282 responds positively in the K5-specific phage typing test according to the method of B. Kaiser et al (J. Clin. Microbiol., (1984), 19, 2, 264–266). It is hence clearly an *Escherichia coli* (K5) strain. This strain was deposited with the CNCM of the Pasteur Institute, Paris, France, under No. I-1013. It is also possible to use a mutant of this strain, either spontaneous or induced, as well as other suitable *Escherichia coli* (K5) strains, for example the strain Bi 626-42 (012:KSEIM ATCC 23508.

The culture medium used is preferably a medium rich in nitrogenous matter, for example a medium rich in yeast extract and in casein hydrolysate, this being an inexpensive means of supplying a large amount of amino acids.

Culturing of the *Escherichia coli* (K5) strain is preferably continued for at least two hours after growth of the biomass has stopped.

The isolation and purification of the N-acetylheparosan, to obtain a composition containing 70% to 100% of an N-acetylheparosan consisting of a mixture of chains of molecular mass between 1500 and 15,000 Da, characterised by a repeated disaccharide structure of formula II, are carried out by a process comprising at least one step of precipitation and one step of ion exchange chromatography. This step is carried out preferably using a Q Sepharose column or an equivalent column. The precipitation is performed with a suitable organic solvent, and in particular an alcohol, preferably ethanol. During this process, the N-acetylheparosan can be in salt form, preferably in the form of a sodium salt.

As an example, the preferred isolation and purification process may be outlined as follows:

step $a_1$: Ethanol precipitation, step $b_1$: Dialysis, step $c_1$: Ethanol precipitation, followed by dehydration and drying, step $d_1$: Purification by anion exchange chromatography, step $e_1$: Ethanol precipitation of the eluate obtained in step $d_1$, dehydration, drying and grinding.

As regards steps $a_1$, $b_1$ and $c_1$, the order in which they are performed is of little importance. One of steps $a_1$ or $c_1$ may be omitted.

In step $e_1$, the ethanol precipitation is not essential. It is possible to isolate the N-acetylheparosan by other methods such as, for example, evaporation under vacuum of the eluate obtained in step $d_1$.

The isolation and purification of the N-acetylheparosan, to obtain a composition containing 70% to 100% of an N-acetylheparosan consisting of a mixture of chains of molecular mass between 1500 and 15,000 Da, may also be performed in the following manner:

step $a'_1$: Dialysis, step $b'_1$: Purification in acid medium, removal of impurities insoluble in aqueous solutions of pH 3.5 and pH 1.8, step $c'_1$: Ethanol precipitation, followed by dehydration and drying, step $d'_1$: Alkaline hydrolysis and dialysis, step $e'_1$: Purification by anion exchange chromatography, step $f'_1$: Purification by exclusion chromatography.

This isolation and purification process is also a preferred process of the invention.

The alkaline hydrolysis is performed with NaOH solution at a temperature of between 30° and 80° C.

In applying the isolation and purification processes, it is possible to use as the starting material either the suspension obtained at the end of culturing, and in this case a prior filtration is necessary, or a product which is already subjected to a preliminary purification performed according to a process which entails the following steps:

step $a''_1$: Centrifugation of the suspension obtained at the end of culturing, step $b''_1$: Bringing the supernatant into contact with an alkaline solution, step $c''_1$: Prefiltration, step $d''_1$: Concentration using a membrane of specified cut-off threshold, step $e''_1$: Dialysis.

Step $e''_1$ is not essential.

As an alkaline solution, 0.1N NaOH solution may be used.

Preferably, a preliminary purification of the product obtained at the end of culturing is performed, according to the method described above.

The culturing of *Escherichia coli* (K5) strains and the isolation and purification processes as well as the preliminary purification step, mentioned above, makes it possible to obtain compositions of N-acetylheparosans containing 70% to 100% of an N-acetylheparosan consisting of a mixture of chains of molecular mass between, 1,500 and 15,000 Da, characterised by a repeated disaccharide structure of formula II:

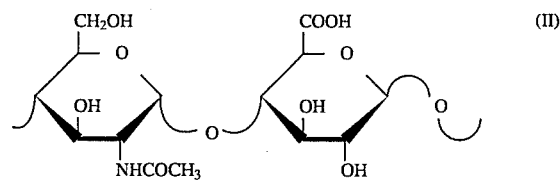

In effect, as a result of the isolation and purification processes described above and the preliminary purification step, it is possible to obtain compositions of N-acetylheparosans containing at least 80% to 100% of an N-acetylheparosan consisting of a mixture of chains of molecular mass between 1,500 and 15,000 Da.

The N-acetylheparosans consisting of a mixture of chains of molecular masses between 1500 and 15,000 Da are new products and also form the subject of the present invention.

The two ends, reducing and non-reducing, of the new N-acetylheparosans as obtained according to the process described above, and using the *Escherichia coli* strain SEBR 3282 or some other suitable strain as stated above, are uronic or N-acetylglucosamine units.

In the majority of the chains, the non-reducing end is a uronic unit of formula (a):

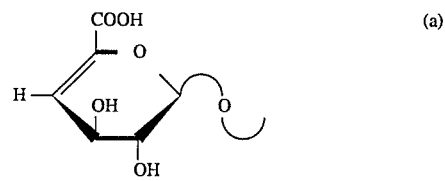

The possible enrichment of the composition obtained with respect to N-acetylheparosan consisting of a mixture of chains of molecular mass between 1500 and 15,000 Da, and having a repeated disaccharide structure of formula II, may be accomplished to various degrees, and in particular up to the point of isolation of the said N-acetylheparosan. The enrichment is carried out by employing conventional molecular mass fractionation techniques such as gel permeation chromatography and ultrafiltration (A. A. Horner, Blochem. J., (1989), 262, 953–958; G. Pyler et al, J. Biol. Chem. (1988), 263, 11, 5197–5201; and U. Lindahl et al, J. Biol. Chem., (1984), 259, 20, 12368–12376). It is also possible to use the ethanol fractionation method (Patent Application EP-A-0,287,477). The latter fractionation method is especially highly valued among other methods which may be contemplated.

The N-acetylheparosans described above are used as intermediates for the preparation of the N,O-sulphated heparosans which are the subject of the present invention, but also for the preparation of other derivatives.

To prepare the N,O-sulphated heparosans which are the subject of the present invention, it is also possible to use other known N-acetylheparosans such as, for example, the N-acetylheparosans consisting mainly of polysaccharide chains all having the same number of disaccharide units, as are described in Patent Application EP-A-0,333,243, and in particular consisting of 6, 8 or 10 "sugar" units, N-acetylheparosan fractions consisting of chains containing on average 10 monosaccharide units (Gupta et al, FEMS Microbiology Letters (1983), 16, 13–17) or high molecular mass N-acetylheparosans which can then be depolymerised according to the methods used for preparing low molecular weight heparins.

In effect, the N,O-sulphated heparosans which are the subject of the present invention may be prepared by other processes from the known polysaccharide (K5) having a high molecular mass. In this case, a depolymerisation step is necessary.

This depolymerisation may be performed before the deacetylation of the high molecular mass N-acetylheparosan, after the deacetylation, after the N-sulphation or alternatively after the N,O-sulphation.

As mentioned above, the depolymerisation may be performed according to the methods described in the literature for preparing low molecular weight heparins, for example by depolymerisation with periodate, with free radicals, by beta-elimination or by the action of nitrous acid (Patent Applications or Patents EP-0,040,144, EP-0,037,319, EP-0,121,067). These methods are given as examples and are not limiting. Any other method of depolymerisation of glycosaminoglycans may be used.

When the N,O-sulphated heparosans are prepared by depolymerisation from a high molecular mass N-acetylheparosan (previously deacetylated and possibly N-sulphated) by subjecting it to the action of nitrous acid, the reducing unit of the N,O-sulphated heparosans which are the subject of the present invention can have a 2,5-anhydromanno, and in particular a 2,5-anhydro-D-mannose, structure. The depolymerisation by the action of nitrous acid may be performed after the N-deacetylation or N-sulphation step. When this step is followed by an oxidation or a reduction, N,O-sulphated heparosans having at the reducing unit a 2,5-anhydro-D-mannonic acid or 2,5-anhydro-D-mannitol structure, respectively, are obtained.

The partial deacetylation of the compositions containing 70% to 100% of N-acetylheparosan, which leads to the production of compositions containing 70% to 100%, and even 80% to 100%, of a heparosan consisting of a mixture of chains of molecular mass between 1500 and 15,000 Da, characterised by a repeated disaccharide structure of formula III described above, is carried out by a treatment with a deacetylating agent.

As deacetylating agents, phosphorus pentasulphide, triethyloxonium fluoroborate, sodium hydroxide or hydrazine may be mentioned, the latter two agents being especially highly valued. It is also possible to use strong mineral acids such as hydrochloric acid, sulphuric acid and the like. The reaction time depends on the working conditions chosen, and in particular on the temperature and the concentration of the deacetylating agent in the reaction medium.

The enrichment of the composition of heparosan with respect to heparosan consisting of chains or of a mixture of chains of molecular mass between 1500 and 15,000 Da, characterised by a repeated disaccharide structure of formula III, is carried out by employing conventional molecular mass fractionation techniques mentioned above (gel permeation chromatography, ultrafiltration and ethanol fractionation). In this case, compositions containing 90% to 100% by mass of a heparosan consisting of a mixture of molecular mass between 1500 and 15,000 Da, having the repeated disaccharide structure of formula III, are obtained.

For the preparation of heparosans consisting of a mixture of chains of molecular masses between 1500 and 15,000 Da, it is also possible to use high molecular weight N-acetylheparosans. The high molecular weight heparosans obtained after deacetylation may be depolymerised by the methods already described for the preparation of low molecular weight heparins and already mentioned in this application. The depolymerisation products can then be subjected to a fractionation in order to obtain the preferred heparosans of the invention.

The heparosans consisting of a mixture of chains of molecular mass between 1500 and 15,000 Da, characterised by a repeated disaccharide structure of formula III:

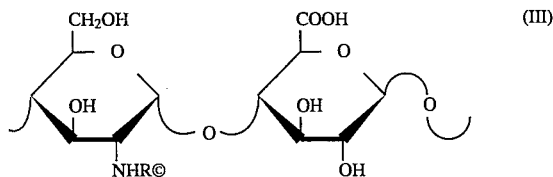

in which R' represents an acetyl group in 0 to 80% of the disaccharide units, and a hydrogen atom in the remaining disaccharide units, are new products and accordingly also form part of the invention.

Preferred heparosans of the invention are heparosans consisting of a mixture of chains of molecular mass between 1500 and 15,000 Da, characterised by a repeated disaccharide structure of formula III in which the acetyl group (R') is present in a content not exceeding 60%.

The compositions of heparosan which contain at least 70% by mass of a heparosan as described above also form part of the present invention.

These heparosans and the compositions of heparosan are useful intermediates for the preparation of the N,O-sulphated heparosans which are the subject of the present invention, but they can also be used for the preparation of other products, for example products which subsequently undergo an epimerisation in the D-glucuronic acid unit.

Before the step of partial N,O-sulphation, the heparosans may be converted to a salt of an organic base or to a quaternary ammonium salt. For the formation of the quaternary ammonium salt of the heparosans, tetrabutylammonium is preferably used.

The step of partial N,O-sulphation carried out according to the process described in French Patent No. 2,584,728 of 10.11.87 (corresponding to Application FR-85/10787) is performed in a polar aprotic solvent such as dimethylformamide, dimethyl sulphoxide, hexamethylphosphoramide or acetonitrile, or a mixture of these solvents, using, for example, a complex of sulphuric anhydride (sulphur trioxide: $SO_3$) with an organic base such as trimethylamine, triethylamine or pyridine. It can also be performed with chlorosulphonic acid dissolved in pyridine. The sulphur trioxide/pyridine complex is preferably used.

It is also possible to use other sulphating agents, in particular those which are reported by E. E. Gilbert in Chemical Review, (1962), 62,549–589. The N,O-sulphation reaction is generally performed at a temperature of between 0° and 100° C., and preferably between 10° and 50° C., for a time between 6 h and 14 h.

During the preparation process, at the end of the partial N,O-sulphation reaction, the composition of N,O-sulphated heparosan containing 70% to 100% of an N,O-sulphated heparosan which is the subject of the present invention is precipitated by adding sodium chloride until a solution which is 0.33M with respect to sodium chloride is obtained, followed by an appropriate amount of ethanol. The precipitate formed is taken up in 0.5M sodium chloride solution. This solution is then neutralised. After the addition of an appropriate amount of ethanol, the precipitate formed is isolated, taken up with ultrapurified water, dialysed against the latter, lyophilised and dried.

The step of N,O-sulphation, as well as the steps of purification of the composition of N,O-sulphated heparosan which are described in the paragraph above, may be repeated one or more times. The purification process is given as an example and does not exclude equivalent processes.

This step of N,O-sulphation is preferably followed by a step of total N-sulphation, carried out in general in an aqueous solvent, advantageously of basic pH, with a sulphating agent such as a complex of sulphuric anhydride with an organic base, for example trimethylamine.

At the end of the step of total N-sulphation, the composition of N,O-sulphated heparosan is precipitated after adding sodium chloride until a solution which is 0.5M with respect to sodium chloride is obtained, and ethanol. The precipitate formed is then redissolved in 0.5M sodium chloride solution, reprecipitated with ethanol, then taken up in ultrapurified water, dialysed against the latter, lyophilised and dried.

The enrichment of the composition of N,O-sulphated heparosan with respect to N,O-sulphated heparosan is carried out by employing the conventional molecular mass fractionation techniques already mentioned. It is advantageous to perform this enrichment.

The N,O-sulphated heparosans which are the subject of the present invention, and the compositions of N,O-sulphated heparosan containing at least 70% of a new N,O-sulphated heparosan which are the subject of the present invention, are advantageously obtained by a process entailing a final N-sulphation reaction. For the repeated structures in the formula (I), E then represents an acetyl group and a sulphate group.

It is also possible to obtain the N,O-sulphated heparosans which are the subject of the present invention by performing first an N-sulphation followed by an O-sulphation. This process variant is preferably used.

The N-sulphation is carried out using a complex of sulphur trioxide with an organic base such as trimethylamine, triethylamine or pyridine. It can also be performed with chlorosulphonic acid dissolved in pyridine. The complex of sulphur trioxide with trimethylamine is advantageously used, and the N-sulphation reaction is carried out at a temperature of between 20° and 80° C. in an alkaline aqueous medium. At the end of the N-sulphation reaction, the product thereby obtained is precipitated by adding an appropriate amount of ethanol. The precipitate formed is taken up with ultrapurified water, dialysed against the latter, lyophilised and dried. The purification process is given as an example and does not exclude equivalent processes. The purification steps may be repeated several times.

According to the process of the invention, before the O-sulphation step, the N-sulphated heparosan is preferably converted to a salt of an organic base or to a quaternary ammonium salt. For the formation of the quaternary ammonium salt, tetrabutylammonium is preferably used.

The O-sulphation reaction is carried out in formamide or another chemically equivalent solvent using, for example, a complex of sulphur trioxide with an organic base such as trimethylamine, triethylamine or pyridine. A sulphur trioxide/pyridine complex is preferably used. The 0-sulphation reaction is in general performed at a temperature of between 10° C. and 50° C.

The N,O-sulphated heparosan is then precipitated by adding sodium chloride to the reaction medium until a solution which is 0.33M with respect to NaCl is obtained, followed by an appropriate amount of ethanol, as in the case of the N,O-sulphation. A purification of the composition of N,O-sulphated heparosan is then performed. The various steps have already been described in detail above (ethanol precipitation, dialysis, and the like).

According to the invention, the preferred N,O-sulphated heparosan contains at least 90% by mass of chains of molecular mass less than 11,000 Da. It is desirable that this N,O-sulphated heparosan should contain less than 0.2 μmol/mg of amino groups ($NH_2$).

The acetyl group is preferably present in a content not exceeding 60%, and it is desirable that the degree of sulphation, expressed as the sulphate/carboxyl ratio, should be between 1.5 and 3.0.

Preferred products of the invention are N,O-sulphated heparosans consisting of chains having an average molecular mass of approximately 4,000 to 7,000 Da and a degree of sulphation, expressed as the sulphate/carboxyl ratio, of between 1.7 and 3, as well as approximately 80% N-deacetylated, N,O-sulphated heparosans (acetyl group content present approximately 20%) consisting of at least by mass of chains of molecular masses between 5,000 and 7,000 Da and having a degree of sulphation of 1.8 to 2.5, or alternatively approximately 80% N-deacetylated, N,O-sulphated heparosans (acetyl group content present approximately 20%) consisting of at least 70% by mass of chains of molecular masses between 10,000 and 12,000 Da and having a degree of sulphation of 1.8 to 2.5, or alternatively approximately 40% N-deacetylated, N,O-sulphated heparosans (acetyl group content present approximately 60%) consisting of at least 70% by mass of chains of molecular masses between 6,000 and 8,000 Da and having a degree of sulphation of 2.0 to 2.8.

Preferred N-sulphated heparosans of the invention are, more especially:

Approximately 80% N-deacetylated, N,O-sulphated heparosans (acetyl group content present approximately 20%) consisting of at least 80% by mass of chains of moleclar masses between 2,300 Da and 7,200 Da and having a degree of sulphation of 1.8 to 2.5, Approximately 80% N-deacetylated, N,O-sulphated heparosans (acetyl group content present approximately 20%) consisting of at least 80% by mass of chains of molecular masses between 3,300 Da and 7,700 Da and having a degree of sulphation of 1.8 to 2.5, Approximately 80% N-deacetylated, N,O-sulphated heparosans (acetyl group content present approximately 20%) consisting of at least 70% by mass of chains of molecular masses between 6,900 Da and 13,500 Da and having a degree of sulphation of 1.8 to 2.5, Approximately 40% N-deacetylated N,O-sulphated heparosans (acetyl group content present approximately 60%) consisting of at least 80% by mass of chains of molecular masses between 4,000 Da and 10,300 Da and having a degree of sulphation of 2.0to2.8.

As salts of N,O-sulphated heparosans, all pharmaceutically acceptable salts are understood. These salts are obtained by conventional methods described, in particular, for the preparation of heparin salts (U.S. Pat. No. 4,168,377).

The process described above for obtaining the N,O-sulphated heparosans together with the purification methods enable the N,O-sulphated heparosans to be obtained in the form of a sodium salt. From these salts, by applying the methods used for preparing the various heparin salts or unsalified heparin ("L'héparine, fabrication, structure, propriétés, analyses" (Heparin, manufacture, structure, properties, analyses), J. P. Duclos, (1984) pp 81–83, Masson Ed. France), it is possible to obtain either other salts of N,O-sulphated heparosans or unsalified N,O-sulphated heparosans.

The N,O-sulphated heparosans which are the subject of the present invention possess advantageous pharmacological and biochemical properties which are altogether suprising in relation to the teachings of the prior art.

In particular, in contrast to the sulphated products of the K5 antigen described in Patent EP-A-0,333,243, which have antiangiogenic and antitumour activity with a favourable ratio of these activities relative to the anticoagulant properties, the N,O-sulphated heparosans of the present invention possess good coagulation-regulatory activity. This activity is very much higher than that of dermatan sulphate with respect to the various parameters of coagulation, and may be compared instead to that of heparin.

More especially, the ATIII- or HCII-dependant anti-IIa activity of representative products of the invention was determined according to the methods described by D. Dupouy et al. in Thrombosis and Haemostasis, (1988), 60, 2,236–239, for heparin cofactor II (HCII) and by M. L. Larsen et al. in Thrombosis Research, (1978), 13, 2, 285–288 for antithrombin (ATIII).

In both cases, the test consists in measuring in vitro the inhibitory effect of the test product on purified thrombin (factor IIa), in the presence of purified HCII or purified ATIII, in the assay of the amidolytic activity of thrombin with respect to a chromogenic substrate. Since it possesses the strongest HCII-dependant anti-IIa activity, dermatan sulphate, prepared according to the method described by H. W. Stuhlsatz et al. in "The Methodology of Connective Tissue Research" (1976) 137–146, is used as a reference product in the test of measurement of this activity, the result being expressed as mg of dermatan sulphate (DS) equivalent in activity to 1 mg of the test product (mg DS equiv/mg).

The anti-Xa activity (Yin-Wessler titre) of the said representative products of the invention was measured by the method described by E. T. Yin et al. in J. Lab. Clin. Med. (1973), 81, 2, 298–310, while their overall anticoagulant activity was measured according to the APTT test described by R. R. Proctor et al. in Am. J. Clin. Path. (1961), 36,212–219.

All the products tested showed an HCII-dependant anti-IIa activity markedly higher than that of dermatan sulphate. The ATIII-dependant anti-IIa activity and the Yin-Wessler titre, although lower than those of heparins, proved higher than those of dermatan sulphate. Their APTT titre is approximately 2- to approximately 20-fold higher than that of dermatan sulphate, and can attain up to 60% of that of heparin.

The N,O-sulphated heparosans of the invention hence exhibit an especially advantageous specificity of action and anticoagulatant activity. The low molecular mass of these products gives them, moreover, pharmacokinetic properties which are also very advantageous.

The N,O-sulphated heparosans of the present invention are of very low toxicity; their toxicity is fully compatible with their use as medicinal products.

The invention hence also extends to pharmaceutical compositions containing as an active principle an N,O-sulphated heparosan which is the subject of the present invention, or one of its salts, or a composition of N,O-sulphated heparosan containing at least 70% of this N,O-sulphated heparosan or one of its salts, in combination with one or more pharmaceutically suitable vehicles.

These pharmaceutical compositions are useful, in particular, for the preventive or curative treatment of disorders of the vascular wall, such as atherosclerosis and arteriosclerosis, and of hypercoagulability states observed, for example, following surgical operations, the development of tumours or disturbances of coagulation induced by bacterial, viral or enzymatic activators.

The dosage can vary widely in accordance with the patient's age, weight and state of health and the nature and severity of the condition, as well as the administration route.

This dosage comprises the administration of one or more doses of approximately 1 mg to 1 g per day, and preferably approximately 5 mg to 500 mg per day, for example of the order of 200 mg per day, intravenously or subcutaneously, administered discontinuously or at regular intervals, or of a daily dose of the order of 200 mg to 1,000 mg per day taken orally.

These doses may naturally be adjusted for each patient in accordance with the observed results and the blood analyses performed beforehand.

The invention is illustrated by the examples below.

N-ACETYLHEPAROSANS

Example 1

Preparation of an N-acetylheparosan preponderantly of low molecular mass (Process I)

1) Culture of the *Escherichia coli* (K5) bacterial strain and separation of a filtrate containing N-acetylheparosan 400 ml of medium B, of composition specified in Table I below, are inoculated with *Escherichia coli* strain SEBR 3282 (deposited with the CNCM of the Pasteur Institute, Paris, France, under No. I-1013), and the suspension is incubated with agitation for 2 h at 37° C.

The preculture obtained is then transferred to an 18.5-l fermenter containing 11 l of medium A, of composition specified in Table I below, and the suspension is incubated for 4 h at 37° C. and pH equal to 7.4, the partial pressure of oxygen being maintained at 40 mmHg by regulating the injection of air (up to 20 l/min) and the agitation. Glucose is then added by introducing a sterile solution containing 600 g/l of glucose in continuous fashion at the rate of 250 ml/h over 8 h.

Culturing is continued under the same conditions of temperature, pH and partial pressure of oxygen for 10 h after the addition of glucose is complete. By monitoring the OD ($\lambda=600$ nm) of the culture medium, it is possible to assert that there is no growth of the biomass during the last 12 hours of culture.

The culture broth is then cooled to 25° C. and thereafter filtered through a membrane of porosity 0.22 µm. Approximately 12 l of filtrate containing N-acetyl-heparosan are thereby obtained.

TABLE 1

| Composition and preparation of medium A and medium B MEDIUM A Medium A is prepared by combining the three sterile solutions below: Solution No. 1 The following are dissolved in order in 700 ml of ultra-purified water: | |
|---|---|
| Complexing agent: N-[tris(hydroxymethyl)methyl]glycine (Tricine marketed by Fluka ®) | 360 mg |
| $FeSO_4 \cdot 7H_2O$ | 280 mg |
| $CaCl_2 \cdot 2H_2O$ | 6.7 mg |
| $MgCl_2 \cdot 6H_2O$ | 1,270 mg |
| $K_2SO_4$ | 500 mg |
| KCl | 5,000 mg |
| Casein hydrolysate (main source of amino acids) HY CASE SF (marketed by Sheffield ®) | 25,000 mg |
| Yeast extract (marketed by Difco ®) | 18,000 mg |
| Solution of trace elements (see Table II below) | 1 ml |

Antifoam agent Struktol J673 (marketed by Schill and Seilacher®): a few drops using a Pasteur pipette. The pH is adjusted to 7.4 with KOH solution (d=1.38) and the volume is made up to 850 ml with ultrapurified water. The medium is autoclaved for 45 min at 120° C.

Solution No. 2

5 g of $K_2HPO_4$ are dissolved in 40 ml of ultrapurified water and the volume is then adjusted to 50 ml with the same solvent. The solution obtained is filtered through a filter of porosity 0.2 μm.

Solution No. 3

20.7 g of glucose are dissolved in an appropriate amount of ultrapurified water and the volume is adjusted to 100 ml with the same solvent. The solution is auto-claved at 110° C. for 30 minutes.

MEDIUM B

The preparation of medium B is identical to that of medium A, apart from the fact that, in addition, 20 g of pH 7.2 buffer (3-morpholinopropanesulphonic acid) should be added after adding the antifoam agent.

TABLE II

Preparation of the solution of trace elements
used in the preparation of medium A and medium B
The following are dissolved (in order) in 800 ml of
ultrapurified water:

| | |
|---|---|
| $H_3BO_3$ | 500 mg |
| $Na_2MoO_4.2H_2O$ | 1,930 mg |
| $CoCl_2.6H_2O$ | 11,850 mg |
| $CuSO_4.5H_2O$ | 25 mg |
| $ZnSO_4.7H_2O$ | 2,000 mg |
| $AlCl_3.6H_2O$ | 2,410 mg |
| 100 ml of hydrochloric acid, density 1.19, are added and the volume is made up to 1,000 ml with ultrapurified water. | |

2) Isolation and purification of an N-acetylheparosan preponderantly of low molecular mass:

Step a—Ethanol precipitation:

Approximately 48 l of 95% ethanol (v/v) are added to the filtrate and the mixture is left to precipitate and settle at 4° C. for 8 h. The supernatant is removed by pumping, followed by centrifugation, and the centrifugation pellet is taken up in approximately 1 l of ultrapurified water.

Step b—Dialysis:

The solution obtained in the preceding step, placed in a NOJAX 40 sack equipped with a cellulose-based membrane of porosity 24 Å, is dialysed for 24 h against ultrapurified water (1 volume of solution/6 volumes of water, renewed after 2 h, 8 h and 16 h). This operation enables small molecules present in the culture medium, such as salts, sugars, amino acids, oligonucleotides and oligopeptides, to be removed.

Step c—Precipitation, dehydration and drying:

0.5M NaCl and 4 volumes of ethanol are added to 1 volume of the dialysed solution. The precipitate is left to form for 5 min at room temperature. The mixture is centrifuged at 5,000 g for 20 min. The centrifugation pellets are taken up in ethanol, and the suspension obtained is stirred and left standing for 1 h at room temperature. The centrifugation and suspension operations are repeated. The mixture is centrifuged again at 5,000 g for 20 min. The centrifugation pellets obtained are dried in an oven under vacuum at 40° C. for 24h.

Step d—Grinding to powder:

The dry centrifugation pellets are ground using a mortar under anhydrous conditions.

Step e—Anion exchange chromatography:

The ground centrifugatgion pellets are taken up in a buffer, referred to as buffer D, of composition 20 mM Tris-HCl pH 7.5, in the proportion of 100 ml/g. The solution obtained is chromatographed on a strong anion exchange column containing a crosslinked agarose matrix with quaternary ammonium groups (Pharmacia R "Q Sepharose Fast Flow"), equilibrated beforehand with buffer D in the proportion of 50 ml of gel per g of powder. The gel is washed with a sufficient amount of buffer D for a return to the baseline of UV detection at 214 nm, and then with a 25 mM piperazine solution whose pH has been adjusted to 3.5. The column is eluted with a solution of pH 3.5 having the compostion 0.5M NaCl and 25 mM piperazine. The eluate is neutralised using 5N NaOH solution.

Step f—Precipitation, dehydration, drying and grinding:

The operations described in steps c and d above are repeated without adding sodium chloride.

The N-acetylheparosan obtained at the end of step f is referred to as batch A.

A variant of the purification process consists in performing steps a, c, b, d, e and f successively. The N-acetylheparosan thereby obtained is referred to as batch B.

3) Characterisation of the N-acetylheparosan obtained at the end of the various purification steps:

Nuclear magentic resonance (NMR) spectrum

The proton and $^{13}C$ carbon NMR spectra are compared with those of the N-acetylheparosan described by W. E. Vann (Eur. J. Biochem., (1981), 116, 59–364).

A study of the spectra obtained with the N-acetylheparosan of batch A and of batch B confirms the chemical identity of the product with the N-acetylheparosan described by W. F. Vann. It comprises polymer chains consisting of repeated β-D-glucuronyl-(1→4)-αN-acetyl-D-glucosaminyl-(1→4)-structures.

Determination of the distribution of molecular masses by exclusion chromatography The distribution of molecular masses is determined by exclusion HPLC under the following conditions:

Column consisting of silica beads 10 μm in diameter and of porosity 250 Å.

Eluent: 0.5M aqueous sodium sulphate solution.

Flow rate: 1 ml/min

UV detection at λ=205 nm.

The calibration is performed using a series of oligosaccharides derived from heparin, of the following molecular masses: 1324, 1883, 2436, 3411, 3996, 4535, 4995, 5365, 6150, 6671, 7542, 8655, 10088, 11561, 12950, 14809, 17387 and 22674 Da.

In view of this series of standards, only molecular masses between 934 Da and 56703 Da are taken into account. It is an accepted fact that the optical density detected is proportional to the amount of N-acetylheparosan. However, the accuracy of the method decreases exponentially for high molecular masses, and in particular those above 20,000 Da.

The elution profile of the exclusion chromatography of batch A is shown in FIG. 1. It is observed on examination of FIG. 1 that the distribution is polydisperse and that it contains a preponderant peak at approximately 4,700 Da. A weight fraction equal to at least 70% of batch A possesses a mass of between 1,700 and 8,000 Da.

A very similar chromatogram is obtained on analysis of batch B. The preponderant peak of the distribution is at approximately 5,000 Da. A weight fraction equal to at least 70% of batch B possesses a molecular mass of between 1,500 and 8,000 Da. Monitoring of the distribution of molecular masses by polyacrylamide gel electrophoresis These samples to be analysed, together with a migration end-marker comprising bromophenol blue, were subjected to electrophoresis in Tris-borate buffer in a 15% polyacrylamide gel obtained by polymerisation of a 29:1 mixture of acrylamide and N,N'-methylenebisacrylamide. Migration is performed under 40 mA for approximately 4 h on a gel 18 cm in length until the migration end-marker emerges. The gel is then stained with alcian blue thereafter with silver according to the technique of S. Pelkonen et al. (J. Bact., (1983), 170, 6, 2646) which is specific for acidic polysaccharides.

This analysis by electrophoresis was performed on the partially purified product obtained at the end of step a and the purified product, batch A or batch B, emanating from the final step, with the object of verifying the absence of substantial modification of the distribution of molecular masses of the N-acetylheparosan during the purification.

Observation of the profiles obtained for the partially purified product obtained at the end of step a and the product purified in the final step (batch A or batch B) does not reveal substantial differences (presence of bands of comparable intensity at the same migration distances). There is hence no substantial modification of the distribution of molecular masses of the N-acetylheparosan during its purification.

Uronic acids assay

The amount of uronic acid per unit mass of the purified product (batch A or batch B) obtained at the end of the final step was determined by colorimetry according to the method described by T. Bitter (Analytical Biochemistry, (1962), 4, 330–334). This assay method is based on the reaction of glycosaminoglycans with carbazole in an acid medium in the heated state, which produces a pink coloration proportional to the amount of uronic acid liberated.

For batch A, the partially purified product obtained at the end of step d and the purified product obtained at the end of the final step f have a uronic acid content of 1.3 and 2.1 µmol/mg, respectively.

For batch B, the purified product at the end of the final step also has a uronic acid content of 2.1 µmol/mg.

Spectrophotometry in the ultraviolet and visible region

The purified product (batch A) is dissolved in ultrapurified water and the solution obtained (C=1 mg/ml) is placed in a cell of 1 cm optical path. Its absorption spectrum is recorded between 200 and 600 nm.

From the spectrum obtained, it is possible to assert, especially on the basis of the absorption at 256 nm, that batch A contains less than 1% of DNA.

Total proteins assay

The "protein assay" kit marketed by BIORAD is used to assay the total proteins. The assay method is based on the fact that the wavelength of maximum absorbence of an acid solution of Coomassie Brilliant Blue G-250 rises from 465 nm to 595 nm when protiens become bound thereto (Reisner et al., Anal Biochem, (1975), 64, 509).

The total proteins content of batch A is less than 1.5%.

Free amino groups ($NH_2$) assay

This assay was performed according to the method described by Zensaku Yosizawa et al. in Biochemica et Biophysica Acta. (1967), 141, 358–365.

The parameter $NH_2$ content (expressed in µmol/mg) is an indicator of the amounts of deacetylated β-D-glucuronyl-(1→4)-α-N-acetyl-D-glucosaminyl-(1→4)-units and contaminants which contain a free amino group.

Batch A and batch B each have an $NH_2$ content of 0.05 µmol/mg. The $NH_2$/glucuronic acid ratio=0.05/2.1 is less than 2.5%. Per 100 β-D-glucuronyl-(1→4)-α-N-acetyl-glucosaminyl-(1→4)-units, there are hence (in mol) fewer than 2.5 disaccharide units of this type which are deacetylated.

EXAMPLE 2

Preparation of an N-acetylheparosan preponderantly of low molecular mass (Process II).

1) Culture of the Escherichia coli (K5) bacterial strain and separation of a filtrate containing N-acetylheparosan The culture of *Escherichia coli* strain SEBR 3282 and the separation of a filtrate containing N-acetylheparosan were carried out according to the method described in Example 1.

2) Isolation and purification of an N-acetylheparosan preponderantly of low molecular mass Step a—Dialysis 375 ml of filtrate are subjected to a dialysis according to the process described in Example 1 [2) Isolation and purification of an N-acetylheparosan preponderantly of low molecular mass, step b]. After dialysis, approximately 1020 ml of purified solution are obtained.

Step b—Purification in an acid medium

An appropriate amount of 5N HCl solution is added to the dialysed solution to obtain a pH equal to 3.5. The precipitate formed is removed by centrifugation and the solution is then acidified with the same acid (5N HCl) to obtain a pH equal to 1.8. A precipitate may form, which will be removed by centrifugation. The solution is then neutralised using 5N NaOH solution.

Step c—Precipitation, dehydration and drying

A suitable amount of sodium chloride is added to the neutralised solution to have a solution which is 0.5M with respect to NaCl, and 4 volumes of ethanol are then added. The precipitate is allowed to form for 5 min at room temperature. The mixture is centrifuged at 5,000 g for 20 min. The centrifugation pellets are taken up in ethanol, and the suspension obtained is stirred and left standing for 1 h at room temperature. The centrifugation and suspension operations are repeated. The mixture is centrifuged again at 5,000 g for 20 min. The centrifugation pellets obtained are dried in an oven under vacuum at 40° C. for 24 h.

Step d—Alkaline hydrolysis and dialysis

The product obtained after drying in the preceding step is dissolved at a concentration of 2.5% (w/v) in 0.25N NaOH solution. The solution thereby obtained is maintained for 2 hours at 50° C. It is then neutralised using 5N HCl solution and the solution containing the polysaccharide is then subjected to a dialysis according to the process described in Example 1 [2) Isolation and purification of an N-acetylheparosan preponderantly of low molecular mass, step b].

After dialysis, approximately 990 ml of solution are obtained.

Step e—Anion exchange chromatography

Appropriate amounts of piperazine, EDTA and Triton X-100 (Prolabo®) are added to the dialysed solution to have concentrations of 25 mM with respect to piperazine, 2 mM with respect to EDTA and 0.2% (v/v) with respect to Triton X-100, respectively. The pH is then adjusted to 3.5 using 5 N HCl solution. This solution is placed on a 400 ml Q Sepharose Fast Flow column equilibrated in a piperazine buffer containing 25 mM piperazine, 2 mM EDTA and 0.2 mM Triton X-100 (pH 3.5). The column is washed with the piperazine buffer and eluted with 0.5M NaCl solution, and the product is then precipitated with 4 volumes of ethanol. It is dried under vacuumat 40° C. Approximately 9.85 g of N-acetylheparosan are thereby obtained.

Step f—Exclusion chromatography 4 g of the product obtained in the preceding stage are dissolved in 60 ml of a buffer solution of composition 20 mM Tris-HCl pH 7.5 and 1M NaCl, and then transferred to a 200 ml Octyl-Sepharose® column equilibrated beforehand with the same buffer. 4 volumes of ethanol are added to the non-retained fraction. The precipitate formed is washed and dried at 40° C. under vacuum.

3.90 g of N-acetylheparosan are thereby obtained.

3) Characterisation of the N-acetylheparosan obtained at the end of the various purification steps Nuclear magnetic resonance (NMR) Spectrum A study of the proton and $^{13}$C carbon NMR spectra obtained with this N-acetylheparosan confirms the chemical identity of the product with the N-acetylheparosan described by W. F. Vann (Eur. J. Biochem. (1981) 116, 59–364).

Determination of the distribution of molecular masses by exclusion chromatography The distribution of molecular masses is determined by exclusion HPLC according to the method used for the determination of the distribution of molecular masses of N-acetylheparosans described in Example 1. A weight fraction equal to at least 86% of the chains which constitute the batch emanating from Example 2 possesses a molecular mass of between 1,500 and 15,000 Da.

Uronic acids assay

The N-acetylheparosan emanating from step e has a uronic acid content of 1.94 μmol/mg.

Spectrophotometry in the ultraviolet and visible region

From the spectrum obtained, it is possible to assert that the N-acetylheparosan obtained contains less than 1% of DNA.

Total proteins assay

The total proteins content of this batch of N-acetylheparosan is less than 1%.

Free amino groups (NH$_2$) assay

The NH$_2$ content is less than 0.1 μmol/mg.

EXAMPLE 3

Preparation of an N-acetylheparosan preponderantly of low molecular mass (Process III)

1) Culture of the Escherichia coli (K5) strain

The culture of *Escherichia coli* strain SEBR 3282 was carried out according to the method described in Example 1. Approximately 12 l of culture containing N-acetylheparosan are obtained.

2) Preliminary purification

Step a—Centrifugation

At the end of culturing, the suspension obtained (12 l) is centrifuged at 8,000 rpm (that is to say between 11,000 and 14,000 g) for 20 min.

Step b—Bringing the medium into contact with an alkaline solution

After the centrifugation, the pellet is removed and the supernatant is brought into contact with 0.1N NaOH solution for approximately 1 hour.

Step c—Prefiltration

The solution obtained in the preceding step is subjected to a prefiltration through a 3M® series 300 polypropylene filter.

Step d—Concentration using a membrane of specified cutoff threshold.

The filtrate obtained in step c is concentrated using an Amicon® hollow-fibre cartridge with a cut-off threshold of 10,000 Da, or equivalent. A solution enriched with respect to low molecular mass N-acetylheparosan is thereby obtained.

Step e—Dialysis

The solution enriched with respect to low molecular mass N-acetylheparosan is dialysed against ultrapurified water, once again using the Amicon® system, to a very high dilution factor (>10,000).

3) Isolation and purification of an N-acetylheparosan preponderantly of low molecular mass:

The procedure used is that described in Example 1 [2) Isolation and purification of an N-acetylheparosan preponderantly of low molecular mass, step c—step f], and an N-acetylheparosan having characteristics similar to those of batch A is obtained, or that described in Example 2 [2) Isolation and purification of an N-acetylheparosan preponderantly of low molecular mass, step a—step f].

N,O-SULPHATED HEPAROSANS

EXAMPLE 4

Chemical modifications of the N-acetylheparosan preponderantly of low molecular mass emanating from Example 1

1) Chemical modifications of batch B

Step a—Partial deabetylation:

500 mg of batch B are dissolved in 10 ml of 1N NaOH solution. The solution is brought to 50° C. and left to react at this temperature for 8 h with stirring. The solution is then neutralised with 2N HCl solution, dialysed against ultrapurified water and then lyophilised.

Step b—Formation of the tetrabutylammonium salt:

The above lyophilisate is taken up in 20 ml of ultrapurified water. The solution obtained is transferred to an ion exchange column based on polystyrene crosslinked with divinylbenzene (Dow Chemical® Dowex 50 W 8), conditioned beforehand in an acid medium so as to regenerate the acid form of the product. The solution is then mixed with 0.4 ml of a 40% tetrabutylammonium solution. It is lyophilised.

Step c—Partial N,O-sulphation:

421 mg of the salt obtained in the preceding step are dissolved in 35 ml of dimethylformamide, and 3.71 g of sulphur trioxide/pyridine complex (marketed by Aldrich® under the ref. S755-6) are added. The mixture is left to react with stirring for 6 h at room temperature. To one volume of the reaction medium, sodium chloride is added until a solution of concentration 0.33M with respect to sodium chloride is obtained, followed by 2 volumes of ethanol. The precipitate is allowed to form. The mixture is centrifuged and the supernatant is removed. The centrifugation pellet is taken up in 0.5M NaCl solution, which is neutralised. 2 volumes of ethanol are then added. The precipitate is allowed to form, the mixture is centrifuged and the centrifugation pellet is taken up with ultrapurified water. The mixture is dialysed against ultrapurified water and lyophilised.

The set of operations described in the above paragraph is repeated.

The lyophilisate obtained possesses the following characteristics:

uronic acid content: 1.11 μmol/mg free NH$_2$ content: 0.01 μmol/mg degree of sulphation: 2.64 per disaccharide unit The uronic acid and NH$_2$ contents are measured as described in Example 1.

The degree of sulphation, also referred to as the sulphate/carboxyl ratio, is the average number of sulphate groups per carboxyl group; it is measured by the conductimetric method of assay of sulphate groups and of carboxyl groups described by B. Casu et al., in Carbohydrate Research, (1975), 39, 168–176.

2) Chemical modifications of batch A

Batch A is divided into three aliquot fractions, referred to as batch A1, batch A2 and batch A3.

Step a—Partial deacetylation and gel filtration:

Batches A1, A2 and A3 were treated as described in step a for batch B above, apart from the fact that only batch A1 is dialysed and lyophilised. Batches A1, A2 and A3 are then fractionated by gel filtration (also referred to as gel permeation chromatography or exclusion chromatography) under the following conditions:

Support of beads 25–75 μm in diameter, based on allyldextran crosslinked with N,N'-methylenebisacrylamide (Sephacryl S-300 HR marketed by Pharmacia®). Eluent used: 0.5M NaCl solution.

Mixtures are made of the fractions corresponding to a Kav of 0.46 to 1 for the heparosan emanating from batch A1, 0.43 to 1 for the heparosan emanating from batch A2 and 0.43 to 0.64 for the heparosan emanating from batch A3. These fractions are referred to below as "gel-filtered heparosans".

Kav is a coefficient customarily used in exclusion chromatography, and enables the fractionation by exclusion chromatography to be reproduced. It is defined by the formula:

$$Kav = \frac{Ve - Vt}{Vo - Vt}$$

in which

Ve=elution volume of the fraction under consideration

Vo=exclusion volume

Vt=total gel volume

The distribution of molecular masses of the heparosan emanating from batch A1 immediately after partial deacetylation, as well as of the gel-filtered heparosans emanating from batches A1, A2 and A3, is determined by exclusion chromatography according to the technique described in Example 1.

Figure 2:
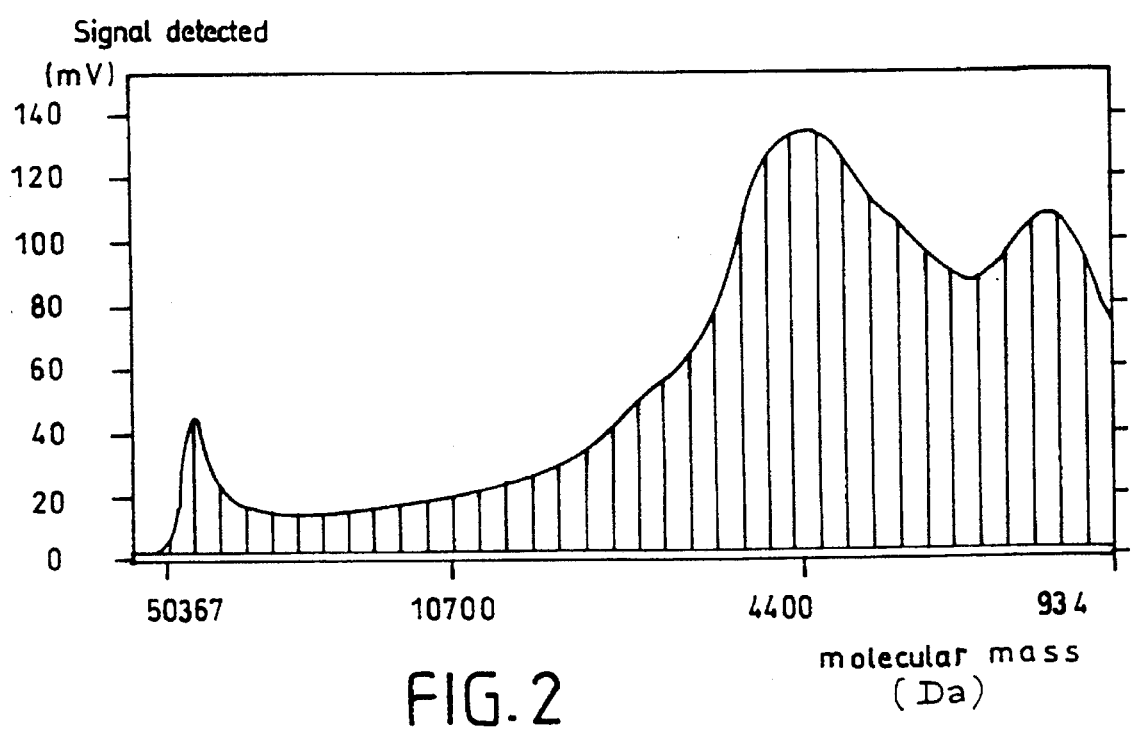
Figure 3:
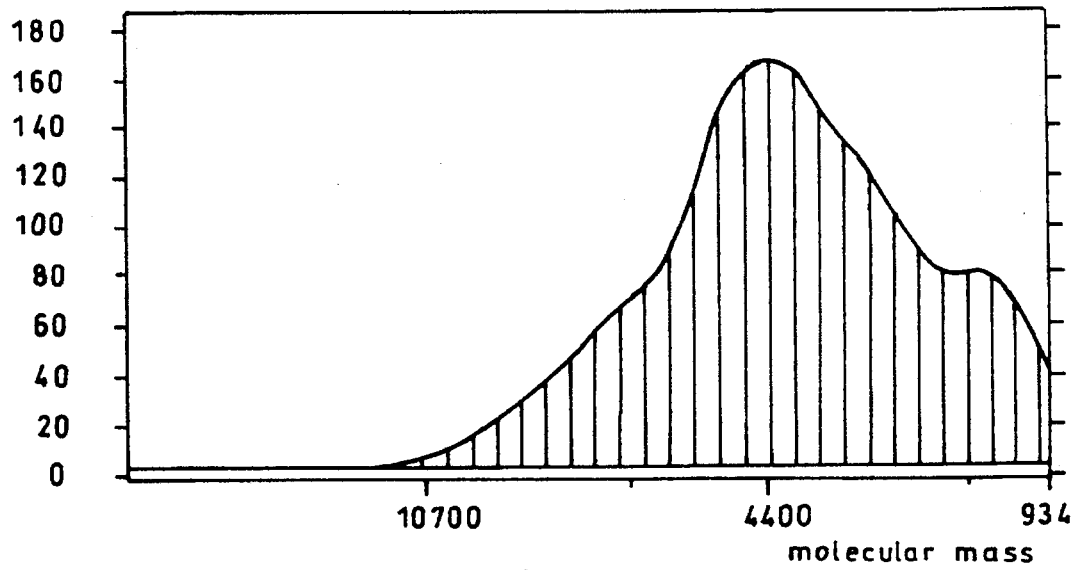

The elution profiles obtained before and after gel filtration for the heparosan emanating from batch A1 are shown in FIGS. 2 and 3, respectively. Some results deduced from the elution profiles are collated in Table III below, in which MWo represents the molecular mass such that a weight fraction of 1% of the product has a molecular mass above Mwo, $Mw_1$ represents the molecular mass such that a weight fraction of 10% of the product has a molecular mass above $MW_1$, $MW_3$ the molecular mass such that a weight fraction of 10% of the product has a molecular mass below $MW_3$, and $MW_2$ represents the molecular mass corresponding to the absorption maximum.

TABLE III

Distribution of molecular masses of the heparosan emanating from batch A1 (not gel-filtered) and of the gel-filtered heparosans emanating from batches A1, A2 and A3

|  | MWo | $MW_1$ | $MW_2$ | $MW_3$ |
|---|---|---|---|---|
| Heparosan, not gel-filtered, emanating from batch A1 | 41,400 | 9,600 | 4,400 | 1,400 |
| Heparosan, gel-filtered, emanating from batch A1 | 10,700 | 6,900 | 4,400 | 1,600 |
| Heparosan, gel-filtered, emanating from batch A2 | 12,700 | 7,000 | 4,500 | 1,500 |

TABLE III-continued

Distribution of molecular masses of the heparosan emanating from batch A1 (not gel-filtered) and of the gel-filtered heparosans emanating from batches A1, A2 and A3

|  | MWo | $MW_1$ | $MW_2$ | $MW_3$ |
|---|---|---|---|---|
| Heparosan, gel-filtered, emanating from batch A3 | 10,300 | 6,900 | 4,500 | 1,500 |

It is observed by comparing FIGS. 2 and 3 that gel filtration enables the less abundant, high molecular mass fraction of the heparosan to be removed.

This result is clearly apparent in Table III, where a large decrease in MWo following the gel filtration operation is observed. The heparosan of each of the batches contains at least 90% by mass of chains of molecular masses less than 7,000 Da.

The gel-filtered heparosans emanating from batches A1 and A2 are then treated as described in Example 1 [2] Isolation and purification of an N-acetylheparosan preponderantly of low molecular mass, step c].

The gel-filtered heparosan emanating from batch A3 is not precipitated, but is dialysed against ultrapurified water.

The uronic acid and free amino groups contents are measured as described in Example 1.

The results obtained are collated in Table IV below. The residual acetyl content was evaluated by considering that there are equal numbers of glucuronyl and glucosaminyl groups.

The degree of deacetylation was calculated as being equal to the ratio of the free amino groups content to the uronic acid content.

Nuclear magnetic resonance spectrum

From a study of the proton nuclear magnetic resonance spectrum obtained with the gel-filtered heparosan emanating from batch A3, it was possible to conclude that the product possesses the expected structure.

The degree of deacetylation calculated by integration was found to be equal to 44%. This value is close to that calculated using the ratio of the free amino groups content to the uronic acid content (41%).

TABLE IV

Characteristics of the gel-filtered heparosans emanating from batches A1, A2 and A3

|  | Uronic acid content assayed (μmol/mg) | $NH_2$ content assayed (μmol/mg) | Calculated residual acetyl content (μmol/mg) | Degree of deacetylation |
|---|---|---|---|---|
| Heparosan, gel-filtered, emanating from batch A1 | 2.3 | 1.10 | 1.20 | 48% |
| Heparosan, gel-filtered, emanating from batch A2 | 2.4 | 1.00 | 1.40 | 42% |
| Heparosan, gel-filtered, emanating from batch A3 | 2.6 | 1.05 | 1.55 | 41% |

Step b—Partial N,O-sulphation:

The gel-filtered heparosans emanating from the deacetylated batches A1, A2 and A3 are treated in the manner described above for batch B (step c, partial N,O-sulphation), apart from the fact that the operations described in the first paragraph are not repeated.

For the heparosan emanating from batch A3, after the first precipitation, the pellet is taken up in ultrapurified water, dialysed against ultrapurified water and left in solution.

The characteristics of the N,O-sulphated products are collated in Table V below:

TABLE V

Characteristics of the N,O-sulphated heparosans emanating from batches A1, A2 and A3 following the partial N,O-sulphation reaction

| | $NH_2$ content (µmol/mg) | Degree of sulphation (sulphate/carboxyl ratio) |
|---|---|---|
| N,O-Sulphated heparosan emanating from batch A1 | 0.10 | 1.9 |
| N,O-Sulphated heparosan emanating from batch A2 | 0.10 | 1.9 |
| N,O-Sulphated heparosan emanating from batch A3 | 0.10 | 1.8 |

It will be noted that, after the N,O-sulphation reaction, the residual $NH_2$ content (0.10 µmol/mg) is greater than that of the purified N-acetylheparosans (0.05 µmol/mg). Sulphation is hence not complete on the nitrogen atom.

Step c—Total N-sulphation:

1 part by weight of N,O-sulphated product, 1 part by weight of sodium bicarbonate and 1 part by weight of the sulphur trioxide/trimethylamine complex are mixed in a volume of 20 ml of ultrapurified water per gram of N,O-sulphated product introduced, and the mixture is left to react at 55° C. with stirring for 20 h. The reaction mixture is then diluted (dilution factor 10), and the conductivity of the solution obtained is thereafter adjusted to that of 0.5M sodium chloride solution. There are then carried out a precipitation by adding 2 volumes of ethanol, a centrifugation followed by taking up the centrifugation pellets with 0.5M NaCl solution and then a second precipitation by adding 2 volumes of ethanol. After being taken up in ultra-purified water and dialysed against ultrapurified water, the products are lyophilised and dried at 40° C. under vacuum.

Nuclear magnetic resonance spectrum

A study of the $^{13}C$ NMR spectrum of the N,O-sulphated heparosan emanating from batch A3 shows that, for this compound, the alcohol at position 6 of the glucosaminyl group is completely in the sulphuric ester form.

Some characteristics of the N,O-sulphated heparosans obtained, determined according to the methods described above, are collated in Table VI below:

TABLE VI

Characteristics of the products obtained following total N-sulphation for batches A1, A2 and A3

| | Uronic acid content (µmol/mg) | $NH_2$ content (µmol/mg) | Degree of deacetylation | Degree of sulphation (sulphate/carboxyl ratio) |
|---|---|---|---|---|
| N,O-Sulphated heparosan emanating from batch A1 | 1.20 | 0.02 | 48% | 2.2 |
| N,O-Sulphated heparosan emanating from batch A2 | 1.30 | 0.02 | 42% | 2.2 |
| N,O-sulphated heparosan emanating from batch A3 | 1.35 | 0.02 | 41% | 2.1 |

It is observed that the residual $NH_2$ content (0.02 µmol/mg) is low, and less than that of the purified N-acetylheparosan (0.05 µmol/mg for batch A and batch B) and also less than that of the N,O-sulphated heparosan obtained following partial N,O-sulphation (specified in Table V). This demonstrates the total nature of the N-sulphation reaction.

The distribution of molecular weights of the products obtained after N-sulphation is analysed by the technique described in Example 1.

Figure 4:
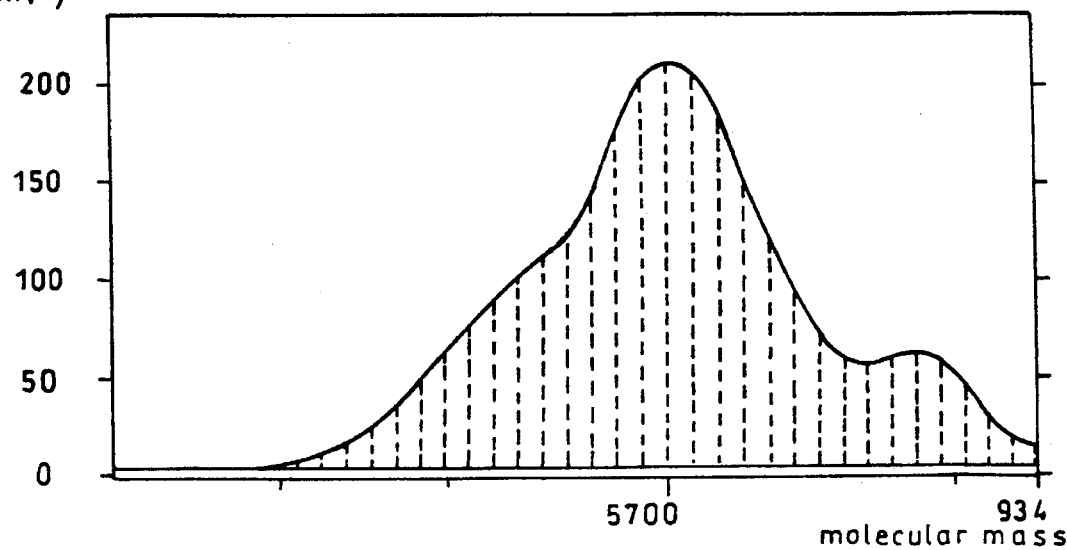

The elution profile obtained for the product emanating from batch A1 is shown in FIG. 4. Very similar elution profiles are obtained for the products emanating from batches A2 and A3.

Some results deduced from the elution profiles are collated in Table VII. The definition of MWo, $MW_1$, $MW_2$ and $MW_3$ is identical to that stated for Table III.

TABLE VII

Distribution of molecular masses of the products obtained following total N-sulphation for batches A1, A2 and A3.

| | MWo | $MW_1$ | $MW_2$ | $MW_3$ |
|---|---|---|---|---|
| Batch A1 | 14,700 | 9,000 | 5,700 | 2,600 |
| Batch A2 | 17,500 | 10,000 | 5,800 | 3,400 |
| Batch A3 | 11,600 | 7,600 | 5,000 | 1,800 |

The N,O-sulphated heparosan of each of the batches contains at least 90% by mass of chains of molecular masses less than 10,000 Da.

In effect, batches A1, A2 and A3 contain 80% of chains of molecular masses between 2,600 Da and % 9,000 Da, 3,400 and 10,000 Da and 1,800 and 7,600 Da, respectively.

EXAMPLE 5

Chemical modifications of the N-acetylheparosan preponderantly of low molecular mass emanating from Example 2. Preparation of N,O-sulphated heparosans: 80% N-deacetylated derivatives The N-acetylheparosan used was prepared according to the process described in Example 2. The uronic acid content of this product is 2.12 µmol/mg. The determination of the distribution of molecular masses was performed by exclusion chromatography according to the method described in Example 1. A weight fraction equal to at least 87.5% possesses chains of molecular masses between 1,500 and 15,000 Da. The preponderant peak of distribution is at approximately 4,900 Da. This batch of N-acetylheparosan is referred to as batch C.

Step a—Partial deacetylation 2.5 g of batch C are dissolved in 50 ml of 2N NaOH solution. The solution is brought to 50° C. and left to react at this temperature for 8 h with stirring. The pH is adjusted to 8 using 2 N HCl solution, and the solution is dialysed against ultrapurified water and then lyophilised.

1.96 g of product are thereby obtained.

Degree of N-deacetylation

The free amino groups ($NH_2$) assay indicates that the N-acetylheparosan has been 80% N-deacetylated.

Step b—N-Sulphation

The above lyophilisate is taken up in 70 ml of water, and 2.5 g of $Na_2CO_3$ and 2.5 g of sulphur trioxide/trimethylamine complex are added. The mixture is left to react for 20 hours at 55° C.

The conductivity of the reaction solution is brought to that of 0.5M NaCl solution by adding demineralised water. Precipitation is induced with 4 volumes of ethanol. The mixture is centrifuged. The precipitate is dissolved again in 0.5M NaCl solution. Precipitation is induced with 4 volumes of ethanol. The mixture is centrifuged.

The centrifugation pellet is taken up with ultrapurified water, and this solution is dialysed according to the process already described (Example 1) and lyophilised.

Approximately 2 g of product are obtained.

Step c—Formation of the tetrabutylammonium salt

The lyophilisate obtained in the preceding step is converted to a tetrabutylammonium salt according to the process described in Example 4 [(1) Chemical modifications of batch B, step b].

2.7 g of salt are obtained.

Step d—O-Sulphation 2.680 g of the salt obtained in the preceding step are dissolved in 196 ml of formamide, and 11.27 g of sulphur trioxide/pyridine complex are added. The mixture is left to react with stirring for 6 hours at 30° C. 1 volume of 2M NaCl solution is added per 5 volumes of reaction solution and the pH is adjusted to 7 using NaOH solution. Reprecipitation is induced with 2 volumes of ethanol, the mixture is centrifuged and the pellet is redissolved in 0.5M NaCl solution. 2 volumes of ethanol are then added. The precipitate is allowed to form, the mixture is centrifuged and the centrifugation pellet is taken up with 80 ml of ultrapurified water. 20 ml of 2M NaCl solution are added, followed by 4 volumes of ethanol. The precipitate is allowed to form and the mixture is centrifuged.

Step e—Gel filtration

The product obtained in step d is taken up with ultrapurified water and then fractionated by gel filtration according to the conditions described in Example 4 [(2) Chemical modifications of batch A, step a]. The molecular masses of the chains which constitute the composition of N,O-sulphated heparosan are determined by exclusion chromatography according to the process described in Example 1. The fractions containing chains having molecular masses of between 1,500 and 12,000 Da [Solution C(A)] are combined on the one hand, and fractions containing N,O-sulphated heparosans composed of chains of molecular masses from Z000 to 30,000 Da [Solution C(M)] are combined on the other hand.

To the solution C(A), 4 volumes of ethanol are added. The precipitate is allowed to form; the mixture is centrifuged and the centrifugation pellet is taken up with ultrapurified water. The mixture is dialysed against ultrapurified water and lyophilised.

1.8 g of product are obtained.

The N,O-sulphated heparosan thereby obtained is referred to as batch C1.

Some characteristics of this N,O-sulphated heparosan, determined according to the methods described above, are collated in Table VIII below.

TABLE VIII

| Characteristics of the product corresponding to batch C1 | | | |
|---|---|---|---|
| Uronic acid content (µmol/mg) | $NH_2$ content (µmol/mg) | Degree of deacetylation | Degree of sulphation (sulphate/carboxyl ratio) |
| Batch C1  1.6 | 0.013 | 80% | 1.9 |

The distribution of molecular weight of the product was evaluated by the technique described in Example 1. Some results deduced from the elution profile are collated in Table IX.

TABLE IX

| Distribution of molecular masses of the product corresponding to batch C1 | | | |
|---|---|---|---|
| MWo | $MW_1$ | $MW_2$ | $MW_3$ |
| Batch C1  9,600 | 7,200 | 5,621 | 2,367 |

The definition of MWo, $MW_1$, $MW_2$ and $MW_3$ is identical to that given in Table III.

The N,O-sulphated heparosan of batch C1 contains by mass of chains between 1,500 and 15,000 Da.

Nuclear magnetic resonance (NMR) spectrum

Proton and $^{13}C$ carbon NMR spectra are obtained with the N,O-sulphated heparosan of batch C1 (spectra run on AMX 500, solvent $D_2O$).

A study of the proton and $^{13}C$ carbon NMR spectra confirms the expected structure of the product. The latter is indeed an N,O-sulphated heparosan.

A study of the ratio of intensity of the sugar protons to that of the acetyl protons in the proton spectrum leads to a proposed degree of deacetylation of 84%. This value is close to that calculated using the ratio of the free amino groups content to the uronic acid content (80%).

The $^{13}C$ carbon NMR spectrum confirms, in particular, that the glucosamine is almost totally N-sulphated. The D-glucuronic acid is not sulphated at positions 2 and 3.

Step f—Gel filtration

To the solution C(M), 4 volumes of ethanol are added. The precipitate is allowed to form, the mixture is centrifuged, the pellet is taken up with ultrapurified water and the mixture is dialysed and lyophilised.

The lyophilisate is then dissolved in 0.5M NaCl solution and fractionated by gel filtration according to the conditions defined in step e.

Fractions containing chains having molecular masses of between 1,300 and 21,000 Da [Solution C(B)] are combined on the one hand, and those from 1,400 to 37,000 Da [Solution C(C)] are combined on the other hand.

These two solutions are treated as described above for the solution C(A) and, after lyophilisation, batch C2 is obtained from the solution C(B) and batch C3 from the solution C(C).

Table X shows some results deduced from the elution profiles for the products of batch C2 and batch C3.

TABLE X

| Distribution of molecular masses of the products corresponding to batches C2 and C3 | | | |
|---|---|---|---|
| | MWo | $MW_1$ | $MW_2$ | $MW_3$ |
| Batch C2 | 14,600 | 9,600 | 7,597 | 5,950 |
| Batch C3 | 28,656 | 17,320 | 10,512 | 7,975 |

The definition of MWo, $MW_1$, $MW_2$ and $MW_3$ is identical to that stated in Table III.

The N,O-sulphated heparosan corresponding to batch C2 contains approximately 99% by mass of chains whose molecular mass is between 1,500 and 15,000 Da, and the N,O-sulphated heparosan corresponding to batch C3 contains approximately 73% by mass of chains whose molecular mass is between 1,500 and 15,000 Da.

EXAMPLE 6

Chemical modifications of the N-acetylheparosan predonderantly of low molecular mass emanating from Example 2. Preparation of an N,O-sulphated heparosan: 40% N-deacetylated derivative having a degree of sulphation of 2.6

The N-acetylheparosan used as a starting material was prepared according to the process described in Example 2. The uronic acid content of this product is 1.96 μmol/mg. This batch is referred to as batch D.

Step a—Partial deacetylation 3.7 g of batch D are dissolved in 74 ml of 1N NaOH, and the mixture is treated according to the process described in Example 5 (step a). The deacetylation is performed under nitrogen.

After lyophilisation, 2.91 g of product are obtained.

Degree of N-deacetylation

The free amino groups ($NH_2$) assay of the product obtained after lyophilisation indicates that the N-acetylheparosan has been 40% N-deacetylated.

Step b—N-Sulphation

The product obtained in the preceding stage was treated with 3.7 g of the sulphur trioxide/methylamine complex in the presence of 3.7 g of $Na_2CO_3$ and according to the process described in Example 5 (step b).

Approximately 3 g of an N-sulphated heparosan is thereby obtained.

Step c—Formation of the tetrabutylammonium salt

Approximately 2 g of the N-sulphated heparosan obtained in the preceding stage are converted according to the method described in Example 5 (step c) to a tetrabutylammonium salt.

2.99 g of lyophilisate are obtained.

Step d—O-Sulphation 2.98 g of the salt obtained in the preceding step are reacted with 14 g of sulphur trioxide/trimethylamine complex according to the process described in Example 5 (step d), and the precipitations and purifications described in this same Example 5 (step d) are then performed.

2.8 g of product are obtained.

Step e—Gel filtration

The product obtained in the preceding step is fractionated by gel filtration using the method and equipment described in Example 4 [2] Chemical modifications of batch A, step a].

The distribution of molecular masses of the N,O-sulphated heparosan fractions is determined by exclusion chromatography according to the technique described in Example 1. The fractions consisting of N,O-sulphated heparosans, the majority of whose chains have a molecular weight of between 1,500 and 15,000 Da, are isolated.

These fractions are then concentrated and subjected to a dialysis against ultrapurified water. A precipitation is then carried out by adding 5 volumes of ethanol, the mixture is centrifuged, the precipitate is dissolved in 0.5M NaCl solution and the precipitation operation is repeated.

The purified product thereby obtained is subjected to a second fractionation using the protocol mentioned at the beginning of this step. The distribution of molecular masses of the fractions is determined by exclusion chromatography according to the method already described. The fractions containing products having molecular masses of between 4,000 and 8,000 Da are collected.

The fractions are subjected to a dialysis and the products are then precipitated by adding ethanol. The precipitate is recovered and dissolved in 0.5M NaCl solution. The solution thereby obtained is dialysed against ultrapurified water and then lyophilised.

Approximately 1 g of an N,O-sulphated heparosan, referred to as batch D1, is thereby obtained.

The characteristics and the distribution of molecular masses of this N,O-sulphated heparosan are shown in Tables XI and XII, respectively.

TABLE XI

| Characteristics of the product corresponding to batch D1 | | | |
|---|---|---|---|
| | Uronic acid content (μmol/mg) | $NH_2$ content (μmol/mg) | Degree of deacetylation | Degree of sulphation (sulphate/ carboxyl ratio) |
| Batch D1 | 1.53 | 0.01 | 40% | 2.60 |

TABLE XII

| Distribution of molecular masses of the product corresponding to batch D1 | | | |
|---|---|---|---|
| | MWo | $MW_1$ | $MW_2$ | $MW_3$ |
| Batch D1 | 15,430 | 10,305 | 6,850 | 4,047 |

The definition of MWo, $MW_1$, $MW_2$ and $MW_3$ is identical to that stated in Table III.

Figure 5:
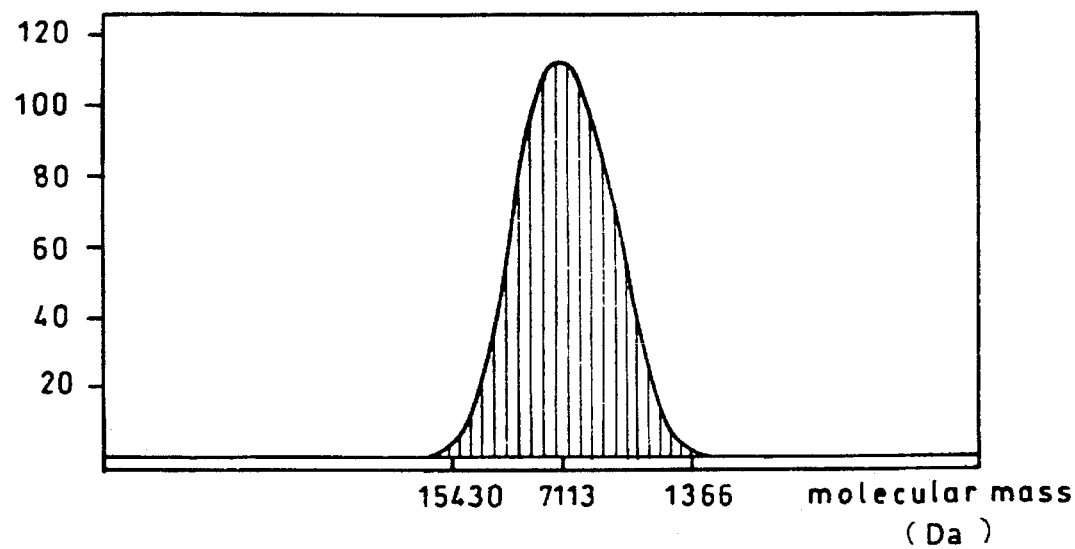

The N,O-sulphated heparosan of batch D1 contains 80% by mass of chains between 4,047 and 10,305 Da, and approximately 98.5% by mass of these chains have a molecular mass of between 1,500 and 14,600 Da. FIG. 5 shows the elution profile obtained for this N,O-sulphated heparosan.

Nuclear magnetic resonance (NMR.) spectrum

Proton and $^{13}C$ carbon NMR spectra are obtained with the N,O-sulphated heparosan of batch D1 (spectra run on AMX 500, solvent $D_2O$).

A study of the proton and $^{13}C$ carbon NMR spectra confirms the expected structure of the product. The latter is indeed an N,O-sulphated heparosan.

The $^{13}C$ carbon NMR spectrum confirms, in particular, that no amino group of the glucosamine unit is in free amino ($NH_2$) form. The glucosamine is completely sulphated at position C6; in contrast, not all the hydroxyl groups of the glucuronic acid are sulphated.

EXAMPLE 7

Chemical modifications of an N-acetylheparosan preponderantly of low molecular mass emanating from Example 2. Preparation of an N,O-sulphated heparosan: 40% N-deacetylated derivative having a degree of sulphation of 3.

As a starting material, a batch of N-acetylheparosan prepared according to the process described in Example 2 is used. This batch is referred to as batch E, and has a uronic acid content of 2 µmol/mg.

The distribution of molecular weight of this N-acetylheparosan was evaluated by the technique described in Example 1. This N-acetylheparosan contains approximately 75% by mass of chains between 1,500 and 15,000 Da, and the average mass of these chains is approximately 10,900 Da. The molecular mass of the preponderant species is 5,135 Da.

Step a—Partial deacetylation

The N-acetylheparosan was 40% N-deacetylated according to the protocol mentioned in Example 6 (step a). To perform this N-deacetylation, 2.5 g of starting material are used, this being dissolved in 50 ml of 1N NaOH. At the end of the reaction, the pH of the reaction medium is adjusted to 6 using HCl and the medium is then concentrated.

Degree of N-deacetylation

The free amino groups ($NH_2$) assay indicates that the N-acetylheparosan has been 40% N-deacetylated.

Step b—Gel filtration

A Sephacryl S-300 HR column (5 cm×100 cm) equilibrated with 0.5M NaCl is used.

The distribution of molecular masses of the heparosan contained in the various fractions is determined by exclusion chromatography. The fractions containing chains having a molecular mass of 6,000 to 20,000 Da are combined, the mixture is concentrated in a rotary evaporator, precipitation is induced with 4 volumes of ethanol and the precipitate formed is dried.

Approximately 1 g of product is thereby obtained.

Step c—Formation of the tetrabutylammonium salt and partial N,O-sulphation

To form the tetrabutylammonium salt, 300 mg of the product obtained in the preceding step are used and the process described in Example 4 [1] Chemical modifications of batch B, step b] is applied. 490 mg of salt are obtained, which salt is dissolved in 30 ml of formamide. A partial N,O-sulphation is then performed according to the process described in Example 4 [1] Chemical modifications of batch B, step c—first paragraph].

From 490 mg of salt which are reacted with 2.25 g of sulphur trioxide/pyridine complex, 406 mg of N,O-sulphated heparosan are obtained.

Step d—Total N-sulphation and gel filtration 372 mg of the product obtained in the above step are dissolved in 15 ml of 5% $Na_2CO_3$ solution and treated with 372 mg of sulphur trioxide/trimethylamine complex according to the method described in Example 4 [2] Chemical modifications of batch A, step c].

The product obtained after total N-sulphation is then fractionated by gel filtration, using a Sephacryl S-300 HR column (2.5 cm×100 cm) and applying the protocol already described.

The fractions having a molecular mass of 6,000 to 20,000 Da are combined, concentrated in a rotary evaporator, dialysed extensively against cold ultra-purified water and lyophilised.

260 mg of an N,O-sulphated heparosan, referred to as batch E1, are thereby obtained.

The characteristics of this product are collated in Table XIII.

Table XIV shows the distribution of molecular masses of chains which constitute batch E1.

This N,O-sulphated heparosan contains approximately 75% by mass of chains of molecular masses between 1500 and 15,000 Da, and approximately 65% by mass of chains having molecular masses of between 7700 and 15,000 Da.

TABLE XIII

| Characteristics of the product corresponding to batch E1 | | | |
|---|---|---|---|
| Uronic acid content (µmol/mg) | $NH_2$ content (µmol/mg) | Degree of deacetylation | Degree of sulphation (sulphate/carboxyl ratio) |
| Batch E1 1.35 | 0.01 | 40% | 3 |

TABLE XIV

| Distribution of molecular masses of the product corresponding to batch E1 | | | | |
|---|---|---|---|---|
| | MWo | $MW_1$ | $MW_2$ | $MW_3$ |
| Batch E1 | 31,238 | 19,671 | 12,029 | 7,748 |

The definition of MWo, $MW_1$, $MW_2$ and $MW_3$ is identical to that stated in Table III.

EXAMPLE 8

Preparation of two batches of an N,O-sulphated heparosan: 80% N-deacetylated derivatives having a degree of sulphation of 2.25 and 2.4

The starting material used, batch F, is a batch of N-acetylheparosan prepared according to the method described in Example 2.

The determination of the distribution of molecular masses of the chains which constitute this compound was carried out by exclusion chromatography according to the method desecribed in Example 1.

From examination of the profile, it is possible to establish that batch F contains 92% by mass of chains whose molecular mass is between 1,500 and 15,000 Da.

The preponderant peak is located at approximately 4800 Da. A weight fraction of batch F equal to at least 80% possesses a molecular mass of between 2,400 and 10,000 Da.

The uronic acid content of this product is 2.4 µmol/mg.

Step a—Partial deacetylation

The procedure is as described in Example 5 (step a), using 2.5 g of batch F and 50 ml of 2N NaOH.

1.6 g of 80% N-deacetylated product are obtained.

The percentage N-deacetylation was evaluated by free amino groups assay.

Step b and c—N-Sulphation and formation of the tetrabutylammonium salt

These two steps are identical to steps b and c described in Example 5.

4.7 g of tetrabutylammonium salt are obtained.

Step d—O-Sulphation 2.9 g of salt obtained above are dissolved in 290 ml of formamide, and 17.4 g of sulphur trioxide/pyridine are added.

The procedure is as described in step d of Example 5.

The pellet obtained after the second centrifugation is dissolved in ultrapurified water, and the mixture is then dialysed against ultrapurified water and lyophilised.

3.68 g of product are thereby obtained.

Step e—Gel filtration

The product obtained in the preceding step is dissolved in 0.5M NaCl solution and then placed on a Sephacryl S-300 HR column equilibrated with 0.5M NaCl. The effluent is collected using a fraction collector.

The fractions having a molecular mass of between 1,400 Da and 10,000 Da are combined and concentrated in a rotary evaporator. Precipitation is induced with 4 volumes of ethanol, the mixture is centrifuged, the precipitate is taken up with ultrapurified water, the solution thereby obtained is dialysed extensively against ultrapurified water and lyophilised and the product is dried.

1.6 g of an N,O-sulphated heparosan, referred to as batch F1, are thereby obtained.

The fractions corresponding to molecular masses of between 5,000 Da and 35,000 Da are combined and concentrated in a rotary evaporator and 4 volumes of ethanol are added to the solution thereby obtained, the mixture is centrifuged, the precipitate is taken up with water and the solution thereby obtained is dialysed against ultrapurified water and lyophilised. The lyophilisate is subjected to a further fractionation according to the method described at the beginning of this step.

The distribution of molecular masses of the various fractions is determined by exclusion chromatography according to the method described in Example 1. The fractions which contain N,O-sulphated heparosans having a molecular mass of between 2,000 and 26,000 Da are combined. Precipitation is induced with 4 volumes of ethanol, the mixture is centrifuged, the pellet is redissolved in distilled water and the mixture is dialysed and lyophilised. 0.6 g of an N,O-sulphated heparosan, referred to as batch F2, is thereby obtained.

The characteristics of batches F1 and F2 are shown in Table XV. Results deduced from the elution profiles are collated in Table XVI.

TABLE XV

Characteristics of the N,O-sulphated heparosans corresponding to batches F1 and F2

| | Uronic acid content (µmol/mg) | $NH_2$ content (µmol/mg) | Degree of deacetylation | Degree of sulphation (sulphate/carboxyl ratio) |
|---|---|---|---|---|
| Batch F1 | 1.58 | <0.01 | 80% | 2.4 |
| Batch F2 | 1.58 | <0.01 | 80% | 2.25 |

TABLE XVI

Distribution of molecular masses of the products corresponding to batches F1 and F2

| | MWo | $MW_1$ | $MW_2$ | $MW_3$ |
|---|---|---|---|---|
| Batch F1 | 10,700 | 7,700 | 5,800 | 3,300 |
| Batch F2 | 24,400 | 16,325 | 8,600 | 6,900 |

The definition of MWo, $MW_1$, $MW_2$ and $MW_3$ is identical to that stated in Table III.

The N,O-sulphated heparosan of batch F1 contains approximately 99% by mass of chains having molecular masses of between 1,500 and 15,000 Da, and that of batch F2 contains approximately 84.6% by mass of chains of molecular masses from 1,500 to 15,000 Da and approximately by mass of chains of molecular masses from 6,000 to 13,500 Da.

Nuclear magnetic resonance (NMR) spectrum

Proton and $^{13}C$ carbon NMR spectra are obtained with the N,O-sulphated heparosan of batch F1 (spectra run on AMX 500, solvent $D_2O$).

A study of the proton spectrum, and in particular of the ratio of intensity of the sugar protons to that of the amino deacetylatedprotons, leads to a proposed value of 20% of N-acetylated glucosamine units.

A study of $^{13}C$ spectrum confirms that the glucosamine unit is indeed N-sulphated. The glucuronic acid, in the majority of the disaccharide structures, is not O-sulphated at positions 2 and 3.

PREPARATIONS

PREPARATION A

Preparation of an N-acetylheparosan preponderantly of high molecular mass (Process I)

1) Culture of the *Escherichia coli* (K5) strain and separation of a filtrate containing N-acetylheparosan 400 ml of medium D, of composition specified in Table XVII below, are inoculated with *Escherichia coli* strain SEBR 3282 and the suspension is incubated with agitation for 2 h at 37° C.

The preculture obtained is then transferred to an 18.5-1 fermenter containing 11 l of medium C, of composition also specified in Table XVII below, and the suspension is incubated for 6 h 30 min at 37° C. and pH equal to 7.2, the partial pressure of oxygen being maintained at 40 mmHg by regulating the injection of air (up to 20 l/ min) and the agitation. Glycerol is then added by introducing a sterile solution containing 500 g/l of glycerol in continuous fashion at the rate of 18 g/h over 16–17 hours.

Culturing is continued under the same conditions of temperature, pH and partial pressure of oxygen until virtually all the glycerol has been consumed. Monitoring of the OD ($\lambda$=600 nm) of the culture suspension after the addition of glycerol is complete shows a stationary state or a state of slight lysis up to the time of stopping the culture at 28–30 h of age in the fermenter.

The culture broth is then cooled to 25° C. and thereafter filtered through a membrane of porosity 0.22 μm. Approximately 12 l of filtrate containing N-acedtylheparosan preponderantly of high molecular mass are thereby obtained.

TABLE XVII

Composition and preparation of medium C and medium D
MEDIUM C
The following are dissolved in order in 900 ml of ultrapurified water:

| | |
|---|---|
| NTA (nitrilotriacetic acid) | 1,000 mg |
| $K_2HPO_4$ | 790 mg |
| Glutamic acid | 11,000 mg |
| $MgCl_2.6H_2O$ | 500 mg |
| $K_2SO_4$ | 450 mg |
| $FeSO_4.7H_2O$ | 18 mg |
| $CaCl_2.2H_2O$ | 2 mg |
| NaCl | 500 mg |
| KCl | 5,000 mg |
| Solution of trace elements (see Table II, Example 1) | 1 ml |
| Glycerol | 10,000 mg |

The pH is adjusted to 7.2 with concentrated potassium hydroxide of density 1.38, and the volume is made up to 1000 ml with ultrapurified water. A sterilising filtration is performed through a 0.2 μm membrane.

Glycerol solution 50 g of glycerol are dissolved in an appropriate amount of ultrapurified water and the volume is adjusted to 1000 ml with the same solvent. A sterilising filtration through a 0.2 μm membrane is performed. The anti foam employed during fermentation is Struktol J 673 (Schill and Sellacher®).

MEDIUM D

The preparation of medium D is identical to that of medium C, apart from the fact that, in addition, the buffer (pH 7.2 ) 3-morpholinopropanesulphonic acid should be added after adding the antifoam agent.

2) Isolation and purification of an N-acetylheparosan preponderantly of high molecular mass The N-acetylheparosan preponderantly of high molecular mass was isolated and purified according to the process described in Example 2 [2 ) Isolation and purification of an N-acetylheparosan preponderantly of low molecular mass, step a—step f].

3) Characterisation of the N-acetylheparosan obtained

Determination of the distribution of molecular masses by exclusion chromatography In view of the standards used at the present time, the distribution of molecular masses was evaluated approximately.

The N-acetylheparosan obtained for this preparation is composed of chains of molecular masses between 20,000 Da and 500,000 Da, and the average mass lies at approximately 100,000–200,000 Da.

Uronic acids assay

The uronic acid content of the purified product at the end of the final step is 2.2 μmol/mg.

Spectrophotometry in the ultraviolet and visible region

From the spectrum obtained, it is possible to assert that this batch contains less than 0.5% of DNA.

Total proteins assay

The total proteins content is less than 0.5%

Free amino groups ($NH_2$) assay

The $NH_2$ content is less than 0.1 μmol/mg.

PREPARATION B

Preparation of an N-acetylheparosan preponderantly of high molecular mass (Process II)

1) Culture of the Escherichia coli (K5) strain

The culture of Escherichia coli strain SEBR 3282 was carried out according to the method described in Preparation A. Approximately 12 l of culture containing N-acetylheparosan preponderantly of high molecular mass are obtained.

2) Preliminary purification

The procedure is as described in Example 3 [2) Preliminary purification], using in stage d an Amicon® hollow-fibre cartridge with a cut-off threshold of 30,000 Da, or equivalent.

3) Isolation and purification of an N-acetylheparosan preponderantly of high molecular mass The procedure is as described in Example 3 [3) Isolation and purification of an N-acetylheparosan preponderantly of low molecular mass].

PREPARATION C

Chemical modifications of the N-acetylheparosan preponderantly of high molecular mass emanating from Preparation A As a starting material for the various chemical modifications, an N-acetylheparosan, referred to as batch G1, prepared according to the process described in Preparation A, is used.

The uronic acid content of this product is 2.41 μmol/mg.

Step a—Partial deacetylation 1.9 g of batch G1 are dissolved in 38.5 ml of 2N NaOH. The solution is brought to 50° C. and left to react at this temperature for 8 hours under nitrogen.

The pH is then adjusted to 8.25 by adding 2N HCl. The mixture is dialysed against ultrapurified water and then lyophilised.

1.6 g of product are thereby obtained.

Degree of N-deacetylation

The free amino groups ($NH_2$) assay indicates that the N-acetylheparosan has been 80% N-deacetylated.

Step b—N-sulphation 1.3 g of the product obtained in the preceding step are dissolved in 57 ml of ultrapurified water, 1.9 g of $Na_2CO_3$ and 1.9 g of sulphur trioxide/trimethylamine complex are added and the mixture is brought to 55° C. for 20 hours. The conductivity of the solution is then adjusted to that of 0.5M NaCl solution by adding demineralised water, and precipitation is induced with 4 volumes of ethanol. The mixture is centrifuged, the pellet is taken up with 0.5M NaCl solution, precipitation is induced with 4 volumes of ethanol and the mixture is centrifuged.

The pellet is dissolved in ultrapurified water and the mixture is dialysed with ultrapurified water according to the process described in Example 1 and then lyophilised.

1.809 g of N-sulphated heparosan are thereby obtained.

Step c—Formation of the tetrabutylammonium salt 800 mg of the product prepared in the preceding step are dissolved in 100 ml of water. This solution is placed on a Dowex 50 W 8 ion exchange column and the procedure used is as described in Example 4 [1) Chemical modifications of batch B, step b].

After lyophilisation, approximately 1.3 g of salt are obtained.

Stage d—O-Sulphation

The salt obtained above is dissolved in 80 ml of formamide, and 5.6 g of sulphur trioxide/pyridine complex are added. The mixture is left to react for 6 hours at 30° C. and 16 ml of 2M NaCl are then added. The mixture is brought to pH 7 and precipitation is induced with 2 volumes of ethanol. The precipitate is taken up with 0.5M NaCl solution, reprecipitation is induced with 2 volumes of ethanol, and the mixture is dialysed against ultrapurified water and concentrated in a rotary evaporator.

Step e—Gel filtration

The concentrated solution obtained in the preceding step is fractionated by gel filtration, using a Sephacryl S-300 HR column and using 0.5M NaCl solution as eluent.

The fractions which correspond to molecular masses of between 10,000 and 500,000 Da are isolated.

2 volumes of ethanol are added and the mixture is then concentrated. The conductivity is then adjusted to that of 0.5M NaCl solution, by adding water.

The fractionation by gel filtration is repeated, and the fractions containing an N,O-sulphated heparosan consisting of chains having average molecular masses of 100,000 to 200,000 Da are collected, as are also the fractions containing an N,O-sulphated heparosan consisting of chains having average molecular masses of approximately 50,000 Da and approximately 12,000 Da.

To each of these three fractions, 5 volumes of ethanol are added, the fractions are subjected to a dialysis against ultrapurified water and the solutions obtained after dialysis are subjected to a lyophilisation.

3 batches of N,O-sulphated heparosan are thereby obtained:

batch G1 is an N,O-sulphated heparosan consisting of chains having an average molecular mass of 100,000 to 200,000 Da. 0.140 g of this batch is isolated.

batch G2 is an N,O-sulphated heparosan consisting of chains having an average molecular mass of approximately 50,000 Da. 0.350 g of this N,O-sulphated heparosan is isolated.

batch G3 is an N,O-sulphated heparosan consisting of chains having an average molecular mass of 12,000 Da. Approximately 0.100 g of this latter batch is isolated.

The characteristics of the three batches of N,O-sulphated heparosan described in this example are collated in Table XVIII.

TABLE XVIII

| | Characteristics of the N,O-sulphated heparosans corresponding to batches G1, G2 and G3 | | | |
|---|---|---|---|---|
| | Uronic acid content (μmol/mg) | NH$_2$ content (μmol/mg) | Degree of deacetylation | Degree of sulphation (sulphate/carboxyl ratio) |
| Batch G1 | 1.48 | <0.01 | 80% | 2.6 |
| Batch G2 | 1.45 | <0.01 | 80% | 2.6 |
| Batch G3 | 1.45 | <0.01 | 80% | 2.6 |

We claim:

1. N,O-sulphated heparosans consisting of chains or of a mixture of chains of molecular mass between 1,500 and 15,000 Da, which consist essentially of repeated disaccharide units of formula I:

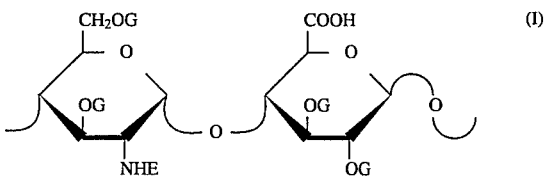

in which:

E represents a group selected from an acetyl group in 0 to 80% of the disaccharide units of the N,O-sulphated heparosans, and a group selected from a sulphate group and a hydrogen atom in the remaining disaccharide units, and G represents a group selected from a hydrogen atom and a sulphate group;

said N,O-sulphated heparosans having a degree of sulphation, expressed as the sulphate/carboxyl ratio, between 1.5 and 3.0; and the pharmaceutically acceptable salts of said N,O-sulphated heparosans.

2. N,O-sulphated heparosans according to claim 1, wherein E represents a group selected from an acetyl group or a sulphate group.

3. N,O-sulphated heparosans according to claim 1, the monosaccharide at the reducing and non-reducing end of the chains of said N,O-sulphated heparosans being selected from optionally sulphated uronic units, optionally sulphated glucosamine units and optionally sulphated N-acetylglucosamine units.

4. N,O-sulphated heparosans according to claim 1, wherein E represents an acetyl group in 0–60% of the disaccharide units of the N,O-sulphated heparosans.

5. N,O-sulphated heparosans according to claim 1, comprising at least 90% by mass of chains of molecular mass less than 11,000 Da.

6. N,O-sulphated heparosans according to claim 1, comprising less than 0.2 μmol/mg of free amino groups.

7. N,O-sulphated heparosans according to claim 1, consisting of chains of average molecular mass approximately 4,000 Da to 7,000 Da and having a degree of sulphation, expressed as the sulphate/carboxyl ratio, of between 1.7 and 3.

8. N,O-sulphated heparosans according to claim 1, comprising at least 70% by mass of chains of molecular masses between 5,000 and 7,000 Da, the degree of sulphation, expressed as the sulphate/carboxyl ration, being between 1.8 and 2.5 and E represents an acetyl group in 0–20% of the disaccharide units of the N,O-sulphated heparosans.

9. N,O-sulphated heparosans according to claim 1, comprising at least 70% by mass of chains of molecular masses between 10,000 and 12,000 Da, the degree of sulphation, expressed as the sulphate/carboxyl ratio, being between 1.8 and 2.5 and E represents an acetyl group in 0–20% of the disaccharide units of the N,O-sulphated heparosans.

10. N,O-sulphated heparosans according to claim 1, comprising at least 70% by mass of chains of molecular masses between 6,000 and 8,000 Da, the degree of sulphation, expressed as the sulphate/carboxyl ratio, being between 2.0 and 2.8 and E represents an acetyl group in 0–60% of the disaccharide units of the N,O-sulphated heparosans.

11. N,O-sulphated heparosans according to claim 1, comprising at least 80% by mass of chains of molecular masses between 2,300 and 7,200 Da, the degree of sulphation, expressed as the sulphate/carboxyl ratio, being between 1.8 and 2.5 and E represents an acetyl group in 0–20% of the disaccharide units of the N,O-sulphated heparosans.

12. N,O-sulphated heparosans according to claim 1, comprising at least 80% by mass of chains of molecular masses between 3,300 and 7,700 Da, the degree of sulphation, expressed as the sulphate/carboxyl ratio, being between 1.8 and 2.5 and E represents an acetyl group in 0–20% of the disaccharide units of the N,O-sulphated heparosans.

13. N,O-sulphated heparosans according to claim 1, comprising at least 70% by mass of chains of molecular masses between 6,900 and 13,500 Da, the degree of sulphation, expressed as the sulphate/carboxyl ratio, being between 1.8 and 2.5 and E represents an acetyl group in 0–20% of the disaccharide units of the N,O-sulphated heparosans.

14. N,O-sulphated heparosans according to claim 1, comprising at least 80% by mass of chains of molecular masses between 4,000 and 10,300 Da, the degree of sulphation, expressed as the sulphate/carboxyl ratio, being between 2.0 and 2.8 and E represents an acetyl group in 0–60% of the disaccharide units of the N,O-sulphated heparosans.

15. A therapeutic composition having an activity for the regulation of coagulation containing an effective amount of a N,O-sulphated heparosan according to claim 1, and a pharmaceutically acceptable excipient, said amount being effective to regulate coagulation.

16. Heparosans consisting of a mixture of chains of molecular mass between 1,500 and 15,000 Da, which consist essentially of a repeated disaccharide structure of formula III:

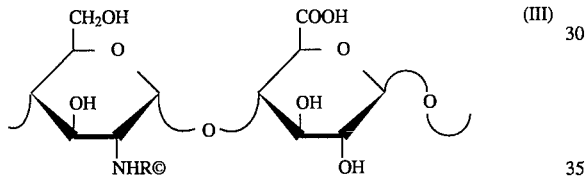

in which R' represents a group selected from an acetyl group in 0 to 80% of the disaccharide units, and a hydrogen atom in the remaining disaccharide units.

17. Heparosans according to claim 16, wherein E represents an acetyl group in 0–60% of the disaccharide units of the N,O-sulphated heparosans.

18. N,O-sulphated heparosans consisting of chains or of a mixture of chains of molecular mass between 1,500 and 15,000 Da, which consist essentially of repeated disaccharide units of formula I:

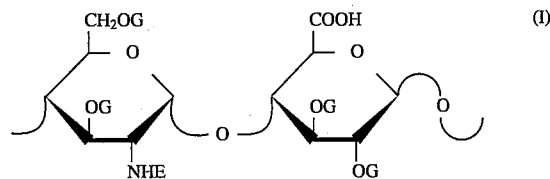

in which:

E represents a group selected from an acetyl group in O to 80% of the disaccharide units of the N,O-sulphated heparosans, and a group selected from a sulphate group and a hydrogen atom in the remaining disaccharide units; and G represents a group selected from a hydrogen atom and a sulphate group, said N,O-sulphated heparosans being obtained by sulphation of heparosans consisting of a mixture of chains of molecular mass between 1,500 and 15,000 Da, which comprise a repeated disaccharide structure of formula III:

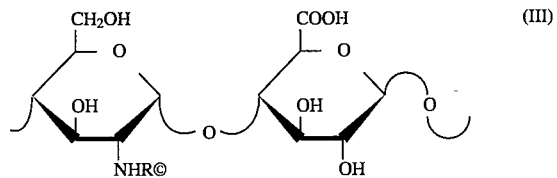

in which R' represents a group selected from an acetyl group in 0 to 80% of the disaccharide units, and a hydrogen atom in the remaining disaccharide units;

said N,O-sulphated heparosans having a degree of sulphation, expressed as the sulphate/carboxyl ratio, between 1.5 and 3.0; and the pharmaceutically acceptable salts of said N,O-sulphated heparosans.

* * * * *